(12) United States Patent
Kobayashi et al.

(10) Patent No.: US 11,162,956 B2
(45) Date of Patent: *Nov. 2, 2021

(54) METHOD AND KIT FOR THE DETECTION OF PANCREATIC DYSFUNCTION

(71) Applicants: TORAY INDUSTRIES, INC., Tokyo (JP); NATIONAL CANCER CENTER, Tokyo (JP)

(72) Inventors: Michimoto Kobayashi, Kamakura (JP); Mitsuaki Sanada, Kamakura (JP); Yoshiyuki Sasajima, Kamakura (JP); Giman Jung, Kamakura (JP); Tesshi Yamada, Tokyo (JP); Kazufumi Honda, Tokyo (JP)

(73) Assignees: TORAY INDUSTRIES, INC., Tokyo (JP); NATIONAL CANCER CENTER, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/555,031

(22) PCT Filed: Mar. 1, 2016

(86) PCT No.: PCT/JP2016/056190
§ 371 (c)(1),
(2) Date: Aug. 31, 2017

(87) PCT Pub. No.: WO2016/140210
PCT Pub. Date: Sep. 9, 2016

(65) Prior Publication Data
US 2018/0031574 A1    Feb. 1, 2018

(30) Foreign Application Priority Data

Mar. 2, 2015 (JP) .............................. JP2015-040580

(51) Int. Cl.
*G01N 33/68* (2006.01)
*C07K 16/18* (2006.01)
*C07K 14/775* (2006.01)
*G01N 33/574* (2006.01)

(52) U.S. Cl.
CPC ....... *G01N 33/6893* (2013.01); *C07K 14/775* (2013.01); *C07K 16/18* (2013.01); *G01N 33/57438* (2013.01); *G01N 2333/775* (2013.01); *G01N 2800/06* (2013.01); *G01N 2800/067* (2013.01)

(58) Field of Classification Search
CPC ......... G01N 33/6893; G01N 33/57438; G01N 2800/067; G01N 2333/775; G01N 2800/06; C07K 16/18
See application file for complete search history.

(56) References Cited

U.S. PATENT DOCUMENTS

| 5,714,350 | A  | 2/1998  | Co et al.         |
| 6,350,861 | B1 | 2/2002  | Co et al.         |
| 7,225,080 | B2 | 5/2007  | Poynard           |
| 2006/0121017 | A1 | 6/2006 | Margolin et al.   |
| 2009/0004671 | A1 | 1/2009 | Yamada et al.     |
| 2010/0130375 | A1 | 5/2010 | Ataman-Onal et al. |
| 2016/0245815 | A1 | 8/2016 | Sanada et al.     |

FOREIGN PATENT DOCUMENTS

| CN | 1468375 A     |   | 1/2004  |             |
| CN | 105637366 A   |   | 6/2016  |             |
| EP | 3054298 A1    |   | 8/2016  |             |
| JP | 2008516965 A  |   | 5/2008  |             |
| JP | 2010120937    | * | 3/2010  | ............ G01N 33/53 |
| JP | 2010175452 A  |   | 8/2010  |             |
| JP | 2010533855 A  |   | 10/2010 |             |
| WO | 9002809 A1    |   | 3/1990  |             |
| WO | WO-9605227 A1 | * | 2/1996  | ........... C07K 14/775 |
| WO | 9702809 A1    |   | 1/1997  |             |
| WO | 9713844 A1    |   | 4/1997  |             |
| WO | 2006098087 A1 |   | 9/2006  |             |
| WO | WO-2007133957 A1 | * | 11/2007 | ........... C12Q 1/6886 |
| WO | 2015050107 A1 |   | 4/2015  |             |
| WO | 2015050107 A1 |   | 3/2017  |             |

OTHER PUBLICATIONS

Campbell (from Monoclonal Antibody Technology, Elsevier Sci Pub. 1984, total 15 pages) (Year: 1984).*
WO 9605227 English Translation (Year: 1996).*
JP 2010120937 English Translation (Year: 2010).*
Raeder et al. (Nature Genetics 2006 vol. 38, p. 54-62). (Year: 2006).*
Honda et al., "Altered Plasma Apolipoprotein Modifications in Patients with Pancreatic Cancer: Protein Characterization and Multi-Institutional Validation", Plos One, Oct. 2012, vol. 7, Issue 10, e46908, pp. 1-11.
Tando et al., "Course: Exocrine Pancreatic Function Test on Bedside", Clinical Gastroenterology, 2008, vol. 23, pp. 513-517; (with partial translation).
Idei et al., "Laboratory Tests in Pancreatic Diseases", Modern Medica, 2008, vol. 54, pp. 180-185; (with partial translation).
Hashimoto, "Rinsho Kensa Data Book", 2013, Igaku_Shoin Ltd., pp. 147-149; (with partial translation).

(Continued)

*Primary Examiner* — Changhwa J Cheu
(74) *Attorney, Agent, or Firm* — Ratnerprestia

(57) ABSTRACT

The purpose of the present invention is to provide a simple and highly accurate method for detecting pancreatic exocrine dysfunction with minimal invasiveness to a subject. The method comprising in vitro measurement of two APOA2 protein variants, mutants thereof and/or fragments thereof in a body fluid sample derived from the subject and detection of the presence or absence of pancreatic exocrine dysfunction on the basis of the measured amounts, and a detection kit for pancreatic exocrine dysfunction including antibodies that can specifically bind to said proteins are provided.

6 Claims, No Drawings

Specification includes a Sequence Listing.

(56) References Cited

OTHER PUBLICATIONS

International Search Report and Written Opinion for International Application No. PCT/JP2016/056190, dated May 31, 2016—6 Pages.

Blanco-Vaca et al., "Role of apoA-II in Lipid Metabolism and Atherosclerosis: Advances in the Study of an Enigmatic Protein", Journal of Lipid Research, vol. 42, 2001, pp. 1727-1739.

Green, M., Molecular Cloning: A Laboratory Manual (4th ed.), Cold Spring Harbor Laboratory Press, Cold Spring Harbor, New York, 2012, 34 Pages.

Holliger et al., "Diabodies: Small bivalent and bispecific antibody fragments", Proc. Natl. Acad. Sci. USA, Jul. 1993, vol. 90, pp. 6444-6448.

Honda et al., "Altered Plasma Apolipoprotein Modifications in Patients with Pancreatic Cancer: Protein Characterization and Multi-Institutional Validation", Plos One, Oct. 2012, vol. 7, Issue 10, pp. 1-11.

Junghans et al., Anti-Tac-H, a Humanized Antibody to the Interleukin 2 Receptor with New Features for Immunotherapy in Malignant and Immune Disorders, Cancer Research, Mar. 1, 1990, vol. 50, pp. 1495-1502.

Marvin et al., "Recombinant approaches to IgG-like bispecific antibodies", Jun. 2005, Acta Pharmacol. Sinica., vol. 26, No. 6, pp. 649-658.

Olafson et al., Covalent disulfide-linked anti-CEA diabody allows site-specific conjugation and radiolabeling for tumor targeting applications, 2004, Protein Engineering, Design & Selection, 2004, vol. 17, No. 1, pp. 21-27.

Rocco AG., et al., "A Model Structure for the Heterodimer apoA-IMilano-apoA-II Supports Its Peculiar Susceptibility to Proteolysis", Oct. 2006, Biophysical Journal, vol. 91, pp. 3043-3049.

Wright et al., "Effect of C2-Associated Carbohydrate Structure on Ig Effector Function: Studies with Chimeric Mousehuman IgG1 Antibodies in Glycosylation Mutants of Chinese Hamster Ovary Cells", Journal of Immunology, 1998, vol. 160, pp. 3393-3402.

Chinese Office Action for Chinese Application No. 201680012702.9, dated Aug. 20, 2018, with translation, 15 pages.

* cited by examiner

SEQUENCE LISTING

```
<160> NUMBER OF SEQ ID NOS: 28

<210> SEQ ID NO 1
<211> LENGTH: 77
<212> TYPE: PRT
<213> ORGANISM: Homo sapiens

<400> SEQUENCE: 1

Gln Ala Lys Glu Pro Cys Val Glu Ser Leu Val Ser Gln Tyr Phe Gln
1               5                   10                  15

Thr Val Thr Asp Tyr Gly Lys Asp Leu Met Glu Lys Val Lys Ser Pro
            20                  25                  30

Glu Leu Gln Ala Glu Ala Lys Ser Tyr Phe Glu Lys Ser Lys Glu Gln
        35                  40                  45

Leu Thr Pro Leu Ile Lys Lys Ala Gly Thr Glu Leu Val Asn Phe Leu
    50                  55                  60

Ser Tyr Phe Val Glu Leu Gly Thr Gln Pro Ala Thr Gln
65                  70                  75

<210> SEQ ID NO 2
<211> LENGTH: 76
<212> TYPE: PRT
<213> ORGANISM: Homo sapiens

<400> SEQUENCE: 2

Gln Ala Lys Glu Pro Cys Val Glu Ser Leu Val Ser Gln Tyr Phe Gln
1               5                   10                  15

Thr Val Thr Asp Tyr Gly Lys Asp Leu Met Glu Lys Val Lys Ser Pro
            20                  25                  30

Glu Leu Gln Ala Glu Ala Lys Ser Tyr Phe Glu Lys Ser Lys Glu Gln
        35                  40                  45

Leu Thr Pro Leu Ile Lys Lys Ala Gly Thr Glu Leu Val Asn Phe Leu
```

```
                    50                  55                  60
Ser Tyr Phe Val Glu Leu Gly Thr Gln Pro Ala Thr
 65                  70                  75

<210> SEQ ID NO 3
<211> LENGTH: 10
<212> TYPE: PRT
<213> ORGANISM: Artificial Sequence
<220> FEATURE:
<223> OTHER INFORMATION: antibody

<400> SEQUENCE: 3

Gly Tyr Thr Phe Thr Asn Tyr Trp Met His
 1               5                  10

<210> SEQ ID NO 4
<211> LENGTH: 17
<212> TYPE: PRT
<213> ORGANISM: Artificial Sequence
<220> FEATURE:
<223> OTHER INFORMATION: antibody

<400> SEQUENCE: 4

Asn Ile Tyr Pro Gly Ser Gly Asn Thr Asn Tyr Asn Glu Lys Phe Lys
 1               5                  10                  15

Ser

<210> SEQ ID NO 5
<211> LENGTH: 10
<212> TYPE: PRT
<213> ORGANISM: Artificial Sequence
<220> FEATURE:
<223> OTHER INFORMATION: antibody

<400> SEQUENCE: 5

Arg Tyr Gly Tyr Val Asp Trp Phe Ala Tyr
 1               5                  10

<210> SEQ ID NO 6
<211> LENGTH: 16
<212> TYPE: PRT
<213> ORGANISM: Artificial Sequence
<220> FEATURE:
<223> OTHER INFORMATION: antibody

<400> SEQUENCE: 6

Arg Ser Ser Lys Ser Leu Leu Tyr Lys Asp Gly Lys Thr Tyr Leu Asn
 1               5                  10                  15

<210> SEQ ID NO 7
<211> LENGTH: 7
<212> TYPE: PRT
<213> ORGANISM: Artificial Sequence
<220> FEATURE:
<223> OTHER INFORMATION: antibody

<400> SEQUENCE: 7

Leu Met Ser Thr Arg Ala Ser
 1               5

<210> SEQ ID NO 8
<211> LENGTH: 9
<212> TYPE: PRT
<213> ORGANISM: Artificial Sequence
<220> FEATURE:
<223> OTHER INFORMATION: antibody
```

<400> SEQUENCE: 8

Gln Gln Leu Val Glu Tyr Pro Leu Thr
1               5

<210> SEQ ID NO 9
<211> LENGTH: 5
<212> TYPE: PRT
<213> ORGANISM: Artificial Sequence
<220> FEATURE:
<223> OTHER INFORMATION: antibody

<400> SEQUENCE: 9

Asn Tyr Gly Met Asn
1               5

<210> SEQ ID NO 10
<211> LENGTH: 17
<212> TYPE: PRT
<213> ORGANISM: Artificial Sequence
<220> FEATURE:
<223> OTHER INFORMATION: antibody

<400> SEQUENCE: 10

Trp Lys Asn Thr Tyr Thr Gly Glu Ser Thr Tyr Ala Asp Asp Phe Lys
1               5                   10                  15
Gly

<210> SEQ ID NO 11
<211> LENGTH: 11
<212> TYPE: PRT
<213> ORGANISM: Artificial Sequence
<220> FEATURE:
<223> OTHER INFORMATION: antibody

<400> SEQUENCE: 11

Arg Asp Gly Ser Lys Tyr Lys Ile Phe Asp Tyr
1               5                   10

<210> SEQ ID NO 12
<211> LENGTH: 12
<212> TYPE: PRT
<213> ORGANISM: Artificial Sequence
<220> FEATURE:
<223> OTHER INFORMATION: antibody

<400> SEQUENCE: 12

Arg Ala Ser Ser Ser Leu Ser Ser Ser Tyr Leu His
1               5                   10

<210> SEQ ID NO 13
<211> LENGTH: 7
<212> TYPE: PRT
<213> ORGANISM: Artificial Sequence
<220> FEATURE:
<223> OTHER INFORMATION: antibody

<400> SEQUENCE: 13

Ser Thr Ser Asn Leu Ala Ser
1               5

<210> SEQ ID NO 14
<211> LENGTH: 9
<212> TYPE: PRT
<213> ORGANISM: Artificial Sequence
<220> FEATURE:

```
<223> OTHER INFORMATION: antibody

<400> SEQUENCE: 14

Gln Gln Phe Ser Val Phe Pro Leu Thr
1               5

<210> SEQ ID NO 15
<211> LENGTH: 10
<212> TYPE: PRT
<213> ORGANISM: Artificial Sequence
<220> FEATURE:
<223> OTHER INFORMATION: antibody

<400> SEQUENCE: 15

Gly Tyr Thr Phe Thr Ser Tyr Trp Met His
1               5                   10

<210> SEQ ID NO 16
<211> LENGTH: 17
<212> TYPE: PRT
<213> ORGANISM: Artificial Sequence
<220> FEATURE:
<223> OTHER INFORMATION: antibody

<400> SEQUENCE: 16

Phe Ile Asn Pro Ser Thr Gly Tyr Thr Glu Asn Asn Gln Arg Phe Asn
1               5                   10                  15

Asp

<210> SEQ ID NO 17
<211> LENGTH: 10
<212> TYPE: PRT
<213> ORGANISM: Artificial Sequence
<220> FEATURE:
<223> OTHER INFORMATION: antibody

<400> SEQUENCE: 17

Arg Pro Tyr Asn Pro Tyr Ala Met Asp Tyr
1               5                   10

<210> SEQ ID NO 18
<211> LENGTH: 11
<212> TYPE: PRT
<213> ORGANISM: Artificial Sequence
<220> FEATURE:
<223> OTHER INFORMATION: antibody

<400> SEQUENCE: 18

Arg Ala Ser Gln Asp Thr Ser Asn Tyr Leu Asn
1               5                   10

<210> SEQ ID NO 19
<211> LENGTH: 7
<212> TYPE: PRT
<213> ORGANISM: Artificial Sequence
<220> FEATURE:
<223> OTHER INFORMATION: antibody

<400> SEQUENCE: 19

Tyr Thr Ser Arg Leu His Ser
1               5

<210> SEQ ID NO 20
<211> LENGTH: 9
<212> TYPE: PRT
<213> ORGANISM: Artificial Sequence
```

```
<220> FEATURE:
<223> OTHER INFORMATION: antibody

<400> SEQUENCE: 20

Gln Gln Gly Asn Thr Leu Pro Tyr Thr
1               5

<210> SEQ ID NO 21
<211> LENGTH: 10
<212> TYPE: PRT
<213> ORGANISM: Artificial Sequence
<220> FEATURE:
<223> OTHER INFORMATION: antibody

<400> SEQUENCE: 21

Gly Tyr Thr Phe Thr Ser Tyr Trp Met His
1               5                   10

<210> SEQ ID NO 22
<211> LENGTH: 17
<212> TYPE: PRT
<213> ORGANISM: Artificial Sequence
<220> FEATURE:
<223> OTHER INFORMATION: antibody

<400> SEQUENCE: 22

Phe Ile Asn Pro Ser Thr Gly Tyr Thr Glu Asn Asn Gln Asn Phe Lys
1               5                   10                  15
Glu

<210> SEQ ID NO 23
<211> LENGTH: 10
<212> TYPE: PRT
<213> ORGANISM: Artificial Sequence
<220> FEATURE:
<223> OTHER INFORMATION: antibody

<400> SEQUENCE: 23

Arg Thr Tyr Asn Pro Tyr Gly Met Asp Tyr
1               5                   10

<210> SEQ ID NO 24
<211> LENGTH: 11
<212> TYPE: PRT
<213> ORGANISM: Artificial Sequence
<220> FEATURE:
<223> OTHER INFORMATION: antibody

<400> SEQUENCE: 24

Arg Ala Ser Gln Asp Ile Ser Asn Tyr Leu Asn
1               5                   10

<210> SEQ ID NO 25
<211> LENGTH: 7
<212> TYPE: PRT
<213> ORGANISM: Artificial Sequence
<220> FEATURE:
<223> OTHER INFORMATION: antibody

<400> SEQUENCE: 25

Tyr Thr Ser Arg Leu Gln Ser
1               5

<210> SEQ ID NO 26
<211> LENGTH: 9
<212> TYPE: PRT
```

```
<213> ORGANISM: Artificial Sequence
<220> FEATURE:
<223> OTHER INFORMATION: antibody

<400> SEQUENCE: 26

Gln Gln Gly Asn Thr Leu Pro Tyr Thr
1               5

<210> SEQ ID NO 27
<211> LENGTH: 16
<212> TYPE: PRT
<213> ORGANISM: Homo sapiens

<400> SEQUENCE: 27

Val Asn Phe Leu Ser Tyr Phe Val Glu Leu Gly Thr Gln Pro Ala Thr
1               5                   10                  15

<210> SEQ ID NO 28
<211> LENGTH: 17
<212> TYPE: PRT
<213> ORGANISM: Homo sapiens

<400> SEQUENCE: 28

Val Asn Phe Leu Ser Tyr Phe Val Glu Leu Gly Thr Gln Pro Ala Thr
1               5                   10                  15

Gln
```

METHOD AND KIT FOR THE DETECTION OF PANCREATIC DYSFUNCTION

CROSS REFERENCE TO RELATED APPLICATIONS

This is the U.S. National Phase application of PCT/JP2016/056190, filed Mar. 1, 2016, which claims priority to Japanese Patent Application No. 2015-040580, filed Mar. 2, 2015, the disclosures of these applications being incorporated herein by reference in their entireties for all purposes.

TECHNICAL FIELD OF THE INVENTION

The present invention relates to a method for detecting pancreatic exocrine dysfunction by measuring the concentrations of two APOA2 isoforms (APOA2-AT or APOA2-ATQ) in body fluid as markers for the detection of pancreatic exocrine dysfunction.

The present invention also relates to a kit for the detection of pancreatic exocrine dysfunction including substances capable of binding to the above proteins for use in the detection of pancreatic exocrine dysfunction.

BACKGROUND OF THE INVENTION

The pancreas is an organ of about 15 cm long located behind the stomach, which has roles in secretion of pancreatic juice containing digestive enzymes required for the digestion of food in the intestinal tract (exocrine function) and in secretion of hormones essential for glucose metabolism, such as insulin and glucagon (endocrine function).

With regard to the exocrine part, plural pancreatic ducts for the transportation of pancreatic juice extend in the pancreas to the duodenum and these pancreatic ducts merge into the main pancreatic duct as they approach the duodenum. The main pancreatic duct merges with the common bile duct just prior to joining the duodenum and then perforates the wall of the duodenum and open into the duodenum at the location called duodenal papilla.

The majority of the digestive enzymes secreted from the pancreas are produced in pancreatic acinar cells as inactive precursor proteins, which are converted to active enzymes through their digestion mediated by peptidases such as pepsin in gastric juice or enterokinase in the brush border of the intestinal epithelium. For example, a precursor enzyme secreted from the pancreas, chymotrypsinogen, is converted to an active enzyme, chymotrypsin, by virtue of trypsin and/or enterokinase. Namely, pancreatic enzymes in the pancreas exist in their inactive forms to prevent the potent degradation enzymes, that is, the pancreatic enzymes from digesting the pancreatic tissue itself. However, when congestion of pancreatic juice occurs in the pancreatic duct due to the blockage of the pancreatic duct and the like, pancreatic enzymes may be converged in the pancreas from the precursor forms to the active forms. Aberrant activation of pancreatic enzymes in the pancreas by such a mechanism causes autodigestion of the pancreas itself and development of pancreatitis.

Exocrine pancreatic function tests are implemented in patients with pancreatic disease such as chronic pancreatitis for the purpose of diagnosing the presence and extent of post-surgical exocrine dysfunction and are generally classified into the categories of tube test and tubeless test.

The tube test is an exocrine pancreatic function test method with high sensitivity and specificity, in which a tube is inserted orally to collect duodenal juice and measure the activity of a pancreatic enzyme. However, the test is invasive and requires complicated procedures to be performed and, moreover, needs a special test apparatus and, disadvantageously, requires much test time and cost. Furthermore, it is difficult in Japan to obtain test reagents which can be administered to human and, thus, implementation of the tube test is difficult.

On the other hand, the tubeless test is a test method, in which the activity of a pancreatic enzyme itself or the amount of a metabolite by the pancreatic enzyme in feces, urine, blood, or exhalation is measured after the substrate for the pancreatic enzyme is ingested along with food or administered orally. For example, currently known examples of a commonly implemented pancreatic function test method include the PFD test, in which a synthetic substrate for chymotrypsin secreted from the pancreas, i.e., BT-PABA (N-benzoyl L-tyrosyl p-aminobenzoic acid) is orally administered and then the concentration of the product of degradation by chymotrypsin, i.e., PABA (p-aminobenzoic acid) in urine is measured; the PLT test, in which a synthetic substrate for elastase secreted from the pancreas, i.e., FDL (Fluorescein dilaurate) is orally administered and then the urinary excretion rate or concentration in blood of the degradation product, i.e., fluorescein is measured; the fecal chymotrypsin test, in which the amount of chymotrypsin in feces is measured; and the fecal elastase test, in which elastase in feces is quantified; and the like. However, in any of the methods, the sensitivity is low and, thus, slight abnormalities are not detectable. Moreover, disadvantageously, those tests require a certain treatment such as dietary restriction before testing and also require hospitalization and a long test time period. Examples of other tubeless tests include a test method in which pancreatic exocrine enzymes that have leaked from the pancreas into blood, such as elastase 1 and pancreatic amylase, are quantified. However, the test method with pancreatic amylase is not effective in the screening of pancreatic exocrine dysfunction despite of its usefulness in the identification of severe pancreatic disease such as acute pancreatitis because an abnormal value for amylase continues to be observed for a short time period, such as several days, after the onset of symptoms and, moreover, the sensitivity of the test is low. On the other hand, the half-life of elastase 1 in blood is relatively longer than that of pancreatic amylase and an abnormal value for elastase 1 continues to be observed for approximately 2 to 4 weeks. However, in pancreatic exocrine dysfunction with significantly reduced pancreatic exocrine function, such as chronic pancreatitis in the decompensated stage, the value of elastase 1 is known to stay in the reference interval for healthy subjects and, thus, is concluded not to be a marker capable of comprehensively detecting pancreatic exocrine dysfunction (Non-Patent Literature 1 to 3). Therefore, there currently is a need for developing a test method for pancreatic exocrine function, the test method imposing a lesser economic burden on a subject and being so sensitive that a highly accurate result is obtained.

APOA2 (Apolipoprotein A2, or Apolipoprotein A-II) protein (GenBank accession No. NP_001634.1) is a member of the apolipoprotein family, which composes plasma lipoproteins. Ten or more apolipoproteins have been identified so far and the major functions of those proteins are to stabilize the lipoprotein structure, to activate the enzymes involved in the lipoprotein metabolism, to function as ligands to the lipoprotein receptors on the cell surface, and the like. The APOA2 protein is one of the apolipoproteins, the components of high density lipoproteins (HDL), which is synthesized in liver tissues as a precursor consisting of 100 amino acids including the signal peptide. The processed mature form of the APOA2 protein present in blood is consisting of 77 amino acids and has a glutamine residue (Q) at the amino-terminus (N-terminus), a threonine residue (T) at position 76 from the N-terminus and a glutamine residue (Q) at position 77 corresponding to the carboxyl-terminus (C-terminus). Moreover, it is reported that APOA2 protein variants having different masses are present, such as the APOA2-ATQ protein which is the full-length APOA2 protein, the APOA2-AT protein which is an APOA2 protein with deletion of the C-terminal glutamine residue (Q), and the APOA2-A protein which is an APOA2 protein with deletion of the C-terminal threonine and glutamine residues (TQ).

According to an analysis based on the three dimensional structural data of the APOA2 protein (PDB ID: 1L6L) recorded in a protein structure databank (Research Collaboratory for Structural Bioinformatics (RCSB) Protein Data Bank (PDB)), APOA2 proteins form a dimer through a disulfide (S—S) bond between cysteine residues located in the N-terminal region. Thus, it is understood that APOA2 proteins are present in blood as dimers having different molecular weights depending on the combination of the above-described three variants. Specifically, a dimer composed of the full-length APOA2-ATQ proteins (the APOA2-ATQ/ATQ protein dimer), a dimer composed of the APOA2-ATQ protein and the APOA2-AT protein (the APOA2-ATQ/AT protein dimer), a dimer composed of the APOA2-AT proteins (the APOA2-AT/AT protein dimer), a dimer composed of the APOA2-AT protein and the APOA2-A protein (the APOA2-AT/A protein dimer), a dimer composed of the APOA2-A proteins (the APOA2-A/A protein dimer) and the like are known. Also, in addition, it is understood that the APOA2 protein forms dimers with other proteins, such as the APOD protein, the APOE protein and the APOA1-M protein, through disulfide linkage and, otherwise, are present as a monomer (Non-Patent Literature 4 and 5).

It is understood that the blood concentrations of the various APOA2 protein dimers described above are significantly different when compared between pancreatic cancer patients and healthy subjects. In particular, the APOA2-ATQ/AT protein dimer has been found, as a result from mass spectrometry, to be a protein having a mass corresponding to a molecular weight of 1725319 (m/z) and indicated to be decreased in pancreatic cancer patients as compared with healthy subjects and to be capable of detecting pancreatic cancer with high accuracy when used as a marker for pancreatic cancer (Patent Literature 1 and 2, Non-Patent Literature 6).

CITATION LIST

Patent Literature

Patent Literature 1: WO2006/098087
Patent Literature 2: JP Patent Publication (Kokai) No. 2010-175452

Non-Patent Literature

Non-Patent Literature 1: Tando et al., 2008, Clinical Gastroenterology, 23: 513-517.
Non-Patent Literature 2: Idei et al., 2008, Modern Media, 54: 180-185.
Non-Patent Literature 3: Rinsho Kensa Data Book, 2013, Igaku-Shoin Ltd., pp. 147-149.
Non-Patent Literature 4: Blanco-Vaca F., et al., 2001, J. Lipid Res., 42: 1727-1739.
Non-Patent Literature 5: Rocco, A G., et al., 2006, Biophys. J., 91: 3043-3049.
Non-Patent Literature 6: Honda, K., et al., 2012, PLoS One, 7: e46908.

SUMMARY OF INVENTION

Technical Problem

Examination of pancreatic exocrine function by a tube test is highly sensitive and specific but highly invasive and unsuitable for screening test in mass examination and the like. Moreover, an exocrine pancreatic function test by a tubeless test, that is, by measuring the activity of a pancreatic digestive enzyme in feces and/or urine is, disadvantageously, prone to be influenced by other digestive system diseases and is less sensitive. Furthermore, although a simple method to detect a pancreatic enzyme present in blood, such as amylase, is available, the sensitivity of the method is low because increase in the concentration of amylase is a transient phenomenon associated with inflammation and the like, and therefore, the method cannot evaluate pancreatic exocrine dysfunction with high accuracy.

Accordingly, an object of the present invention is to provide a simple test method to measure the blood concentrations of proteins for examining pancreatic exocrine dysfunction with high accuracy, the method characterized by imposing a lesser burden on a subject and being less invasive.

Solution to Problem

In order to solve the above-described problems, the inventors first quantitatively detected two out of the APOA2 protein variants, namely the APOA2-AT protein and the APOA2-ATQ protein, and then compared test subjects having pancreatic exocrine dysfunction and normal subjects for the amount of each protein. Then, the amounts of both the proteins in blood were found to be different between the normal subjects and the test subjects having pancreatic exocrine dysfunction. Furthermore, the inventors found that test subjects showing, among other symptoms of pancreatic exocrine dysfunction, disturbance of pancreatic juice flow in the pancreatic duct had a lower blood concentration of APOA2-ATQ than the normal subjects, and that test subjects showing, among other symptoms of pancreatic exocrine dysfunction, insufficient production of pancreatic juice in the pancreatic tissue had a blood concentration of APOA2-ATQ equal to or more than that in the normal subjects while the test subjects had a lower blood concentration of APOA2-AT than the normal subjects.

The present invention encompasses the following inventions, based on the above findings.
(1) A method for detecting pancreatic exocrine dysfunction, the method comprising measuring in vitro the amount of APOA2-ATQ protein or APOA2-AT protein present in body fluid of a test subject, and determining the presence or absence of pancreatic exocrine dysfunction on the basis of the measured amount.
(2) The method for detecting pancreatic exocrine dysfunction according to (1), wherein the APOA2-ATQ protein is a polypeptide consisting of the amino acid sequence represented by SEQ ID NO: 1.

(3) The method for detecting pancreatic exocrine dysfunction according to (1), wherein the APOA2-AT protein is a polypeptide consisting of the amino acid sequence represented by SEQ ID NO: 2.
(4) The method for detecting pancreatic exocrine dysfunction according to any of (1) to (3), wherein, when the amount of the APOA2-ATQ protein in the test subject is smaller than that in normal subjects, the test subject is evaluated to have a pancreas affected by disturbance of pancreatic juice flow.
(5) The method for detecting pancreatic exocrine dysfunction according to (4), wherein the amount of the APOA2-ATQ protein in the test subject is not more than half of that in the normal subjects.
(6) The method for detecting pancreatic exocrine dysfunction according to any of (1) to (3), wherein, when the amount of the APOA2-ATQ protein in the test subject is equal to or more than that in the normal subjects and the amount of the APOA2-AT protein in the test subject is smaller than that in the normal subjects, the test subject is evaluated to have a pancreas affected by insufficient production of pancreatic juice.
(7) The method for detecting pancreatic exocrine dysfunction according to (6), wherein the amount of the APOA2-AT protein in the test subject is not more than half of that in the normal subjects.
(8) The method for detecting pancreatic exocrine dysfunction according to any of (1) to (7), wherein the body fluid sample is blood.
(9) The method for detecting pancreatic exocrine dysfunction according to any of (1) to (8), the method comprising the steps of: measuring the amount of the APOA2-ATQ protein in the sample by using an APOA2-ATQ terminus-binding molecule which specifically binds to the C-terminal region of the APOA2-ATQ protein consisting of the amino acid sequence represented by SEQ ID NO: 1, and an APOA2 non-terminus-binding molecule which binds to the amino acid sequence of the protein excluding the C-terminal region; or measuring the amount of the APOA2-AT protein in the sample by using an APOA2-AT terminus-binding molecule which specifically binds to the C-terminal region of the APOA2-AT protein consisting of the amino acid sequence represented by SEQ ID NO: 2, and the APOA2 non-terminus-binding molecule which binds to the amino acid sequence of the protein excluding the C-terminal region.
(10) The detection method according to (9), wherein the APOA2-ATQ terminus-binding molecule and the APOA2-AT terminus-binding molecule are antibodies or nucleic acid aptamers.
(11) The detection method according to (10), wherein the APOA2-ATQ terminus-binding molecule and the APOA2-AT terminus-binding molecule are an anti-APOA2-ATQ terminus antibody and an anti-APOA2-AT terminus antibody, respectively.
(12) A kit for the detection of pancreatic exocrine dysfunction, comprising an anti-APOA2-ATQ terminus antibody, an anti-APOA2-AT terminus antibody, and/or chemically modified derivatives thereof.
(13) A kit for the detection of pancreatic exocrine dysfunction, comprising one or more of a monoclonal antibody or a fragment thereof selected from the group consisting of an anti-APOA2 terminus monoclonal antibody or a fragment thereof and an anti-APOA2 non-terminus monoclonal antibody or a fragment thereof, wherein: the anti-APOA2 terminus monoclonal antibody specifically binds to the C-terminal region of the APOA2-ATQ protein consisting of the amino acid sequence represented by SEQ ID NO: 1, has the CDR1, CDR2 and CDR3 of the heavy chain consisting of the amino acid sequences represented by SEQ ID NOs: 3, 4 and 5, or SEQ ID NOs: 9, 10 and 11, respectively, and has the CDR1, CDR2 and CDR3 of the light chain consisting of the amino acid sequences represented by SEQ ID NOs: 6, 7 and 8, or SEQ ID NOs: 12, 13 and 14, respectively; and the anti-APOA2 non-terminus monoclonal antibody specifically binds to the amino acid sequence of the APOA2-ATQ protein consisting of the amino acid sequence represented by SEQ ID NO: 1 or the APOA2-AT protein consisting of the amino acid sequence represented by SEQ ID NO: 2, excluding the C-terminal region, has the CDR1, CDR2 and CDR3 of the heavy chain consisting of the amino acid sequences represented by SEQ ID NOs: 15, 16 and 17, or SEQ ID NOs: 21, 22 and 23, respectively, and has the CDR1, CDR2 and CDR3 of the light chain consisting of the amino acid sequences represented by SEQ ID NOs: 18, 19 and 20, or SEQ ID NOs: 24, 25 and 26, respectively.

This specification incorporates the disclosure of Japanese Patent Application No. 2015-040580, which is the basis of priority of this application.

Advantageous Effects of Invention

According to the present invention, pancreatic exocrine dysfunction can easily be detected with high fidelity. Just by measuring the concentrations of two APOA2 protein isoforms contained in a body fluid sample from a test subject, it can be easily determined whether or not the test subject has pancreatic exocrine dysfunction, or which category, in cases where the test subject has pancreatic exocrine dysfunction, the dysfunction falls under, disturbance of pancreatic juice flow or insufficient production of pancreatic juice.

DESCRIPTION OF EMBODIMENTS

1. Markers for the Detection of Pancreatic Exocrine Dysfunction (Outline)

The present invention is based on new findings in the field of pancreatic exocrine dysfunction that in patients with pancreatic disease involving insufficient production of pancreatic juice, the amount of the APOA2-AT protein in blood is smaller than that in healthy subjects and the amount of the APOA2-ATQ protein in blood is equal to or more than that in healthy subjects, and that in patients with pancreatic disease involving disturbed flow of pancreatic juice, the amount of the APOA2-ATQ protein in blood is smaller than that in healthy subjects.

(Constitution)

In this specification, the term "marker for the detection of pancreatic exocrine dysfunction" refers to a biological marker (so-called biomarker) for detecting pancreatic exocrine dysfunction, which is a substance functioning as an index indicating the presence or absence of exocrine dysfunction in the pancreas of a test subject. Pancreatic exocrine dysfunction in a test subject can be detected on the basis of the measurement of the amounts of markers for the detection of pancreatic exocrine dysfunction in blood of the test subject and the comparison of the resulting measured value with the measured value from normal subjects.

The markers for the detection of pancreatic exocrine dysfunction are composed of two APOA2 protein variants, that is, the APOA2-ATQ protein and the APOA2-AT protein, or fragments thereof.

In this specification, the term "pancreatic exocrine function" refers to a function that allows pancreatic juice containing digestive enzymes produced by pancreatic acinar cells in the pancreas to be secreted from the pancreas to the duodenum. The term "pancreatic juice" represents an alkaline digestive juice secreted from the pancreas to the duodenum. The pancreatic juice contains bicarbonate salts secreted from the duct part and a variety of digestive enzymes for the digestion of food produced in pancreatic acinar cells, such as carbohydrate-degrading enzymes and protein-degrading enzymes (amylase, lipase, protease, carboxypeptidase, and the like).

Moreover, in this specification, the term "pancreatic exocrine dysfunction" refers to a condition in which the secretion of pancreatic juice from the pancreas to the duodenum has been reduced. The types of pancreatic exocrine dysfunction include "disturbance of pancreatic juice flow," in which congestion of pancreatic juice occurs in the pancreatic duct due to the blockage of the pancreatic duct, and "insufficient production of pancreatic juice," in which the production of pancreatic juice in pancreatic acinar cells is decreased.

It is understood that pancreatic exocrine dysfunction is induced by the development of various pancreatic diseases such as chronic pancreatitis, pancreatic tumor, and pancreatolithiasis.

For example, chronic pancreatitis is classified into three stages based on its progress: the compensatory stage, the decompensated stage, and a middle stage between them, that is, the transitional stage; and different types of pancreatic exocrine dysfunction are induced according to the progress of the disease. In the compensatory stage, which corresponds to the early phase of the disease, the pancreatic duct is obstructed due to a pancreatic duct stricture or by pancreatic calculi, leading to the block of pancreatic juice flow. Consequently, the pressure inside the pancreatic duct is elevated, leading to the leakage of pancreatic digestive enzymes into blood. In pancreatic exocrine dysfunction in this stage, mild symptoms accompanied by abdominal pain and/or dorsal pain emerge. However, because the pancreas still retains the ability to produce pancreatic juice, the removal of the stricture or pancreatic calculi by therapeutic endoscopy can treat the pancreas and recover its function. On the other hand, in the decompensated stage, pancreatic enzymes staying in the pancreatic duct are activated and, consequently, promote the destruction of the pancreatic parenchyma by autodigestion. Thus, the ability to produce pancreatic juice is significantly adversely affected and pancreatic exocrine dysfunction is manifested. Maldigestion of food is a major symptom in this stage and in some cases it causes pancreatic diabetes as a complication in conjunction with pancreatic endocrine dysfunction.

Chronic pancreatitis can be diagnosed by imaging techniques, such as ultrasound, CT, MRI, and the like. When characteristic graphical observations such as pancreatic calculi in the pancreatic duct and characteristic histological observations such as loss and fibrosis of the pancreatic parenchyma are obtained, a subject exhibiting those features is determined to have chronic pancreatitis. When characteristics histological observations are not detectable, chronic pancreatitis is diagnosed on the basis of repeated occurrence of upper abdominal pain, the values of pancreatic enzymes in blood/urine, the value of the BT-PABA test, and the like.

Moreover, pancreatic exocrine dysfunction also occurs in association with pancreatic ductal carcinoma, which arises from pancreatic ductal epithelial cells. It is understood that this is due to the induction of concomitant pancreatitis from a pancreatic duct stricture caused by pancreatic ductal carcinoma.

Furthermore, pancreatic exocrine dysfunction is allowed to progress or to be ameliorated with a treatment for patients with pancreatic disease. Examples of the treatment for patients with pancreatic disease include improvement in lifestyle behaviors such as dietary therapy, pancreatectomy, radiation therapy, chemotherapy, and the like. For example, standard treatment methods for chronic pancreatitis of mild to moderate severity include dietary therapy including moderation of alcohol intake, low-fat diet, and dietary protein restriction, and/or relief from psychological stress. If necessary, extracorporeal shock wave lithotripsy or therapeutic endoscopy for pancreatic calculi and drainage therapy for pancreatic duct stricture or pancreatic pseudocyst are performed. For acute exacerbations of more advanced chronic pancreatitis and acute pancreatitis, in addition to the dietary therapy described above, sufficient fluid infusion in the early period as well as administration of an analgesic drug for the amelioration of abdominal pain and proteinase inhibitors to reduce the activity of pancreatic enzymes are performed. On the other hand, for the treatment of pancreatic tumor including pancreatic ductal carcinoma, treatment by pancreatectomy is first considered. Particularly, for pancreatic ductal carcinoma, surgical removal of the pancreas is considered to be a sole curative therapy. However, for pancreatic ductal carcinoma unresectable because of the influence of arterial infiltration and the like, chemotherapy using gemcitabine and the like or radiation therapy is performed. In some cases, according to the results of these treatments, insufficient production of pancreatic juice may be induced due to the damage on pancreatic juice-producing cells, or, on the contrary, the disturbance of pancreatic juice flow may be resolved due to the removal of a blockage of the pancreatic duct. In the period after the treatment of the pancreatic disease, it is evaluated whether or not insufficient production of pancreatic juice has been induced in the pancreas after the treatment and, then, the necessity to administer pancreatic enzyme supplements and/or the amounts thereof to be administered are determined.

In this specification, the term "test subject" refers to a specimen as a target for the detection of pancreatic exocrine dysfunction, which is a vertebrate, preferably a mammal, particularly preferably human. In this specification, when a test subject is a human, hereinafter, the test subject is specially referred to as "subject".

In this specification, the term "normal subject" refers to an individual which at least does not have pancreatic exocrine dysfunction, preferably a healthy individual. The normal subject is required to be from the same organism as the test subject. For example, when a test subject examined for the detection is a human (a subject), a normal subject should also be a human (hereinafter in this specification referred to as "healthy subject"). Preferably, the physical conditions of the normal subject are identical or similar to those of the test subject. In the case of human, for example, physical conditions include race, gender, age, height, weight and the like.

In this specification, "APOA2 protein" refers to the APOA2 protein of each species, preferably the APOA2 protein from human (GenBank accession No. NP_001634.1). Specific examples of the APOA2 protein include variants of the wild-type APOA2 protein derived from human and consisting of the amino acid sequence represented by SEQ ID NO: 1 or 2, naturally-occurring mutants thereof, and fragments thereof.

In this specification, the term "APOA2 protein variants" means different molecular forms of the APOA2 protein that can be present in blood (including plasma and serum) or other body fluid of human or animals. For example, the term refers to APOA2 proteins with a different structure in the C-terminal region or naturally-occurring mutants thereof. Specifically, the term refers to, for example, those APOA2 protein variants, such as the APOA2-ATQ protein comprising the C-terminal region having an amino acid sequence that ends in ATQ which consists of the amino acid sequence represented by SEQ ID NO: 1 and, the APOA2-AT protein comprising the C-terminal region having an amino acid sequence that ends in AT which consists of the amino acid sequence represented by SEQ ID NO: 2, and the APOA2-A protein comprising the C-terminal region having an amino acid sequence that ends in A.

In this specification, the term "naturally-occurring mutant" refers to a mutant existing in the natural environment, such as a mutant having the amino acid sequence represented by SEQ ID NO: 1 or 2 except that one or plural amino acids are deleted, substituted, or added, and a mutant having an amino acid sequence with an amino acid identity of 90% or more, 92% or more, or 94% or more, preferably 95% or more, or 96% or more, more preferably 97% or more, further preferably 98% or more, or 99% or more, to the above-described amino acid sequence. The term "amino acid identity" refers to the ratio (in percent) of the number of identical amino acid residues in one amino acid sequence to the total number of amino acid residues (including gaps) in the other amino acid sequence, when the two amino acid sequences are aligned with introducing gaps, if necessary, for maximum correspondence. The term "plural" refers to an integer from 2 to 10, such as an integer from 2 to 7, from 2 to 6, from 2 to 5, from 2 to 4, or from 2 to 3. Specific examples of the naturally-occurring mutants include mutants based on the polymorphisms such as SNPs (single nucleotide polymorphisms), splicing mutants (splicing variants) and the like. Moreover, the above-described substitution is preferably a conservative amino acid substitution. The conservative amino acid substitution is preferable because it allows a variant carrying that type of substitutions to have a structure and characteristics similar to those of the APOA2 proteins having the above-described amino acid sequences. Conservative amino acid means the relationship among amino acids classified into the same amino acid group. In the above-described amino acids, the following groups are known: non-polar amino acid group (glycine, alanine, phenylalanine, valine, leucine, isoleucine, methionine, proline, tryptophan), polar amino acid group (amino acids except for non-polar amino acids), charged amino acid group (acidic amino acid group (aspartic acid, glutamic acid) and basic amino acid group (arginine, histidine, lysine), uncharged amino acid group (amino acids except for charged amino acids), aromatic amino acid group (phenylalanine, tryptophan, tyrosine), branched amino acid group (leucine, isoleucine, valine), and aliphatic amino acid group (glycine, alanine, leucine, isoleucine, valine), etc.

The above-described "fragments thereof" refer to fragments of the APOA2 protein variants and mutants thereof, including the C-terminal regions of the various APOA2 protein variants and naturally-occurring mutants thereof. Specifically, the term refers to protease digests of various APOA2 protein variants and mutants thereof, and the like.

2. Anti-APOA2 Antibodies and Fragments Thereof 2-1. Anti-APOA2 Antibodies

Examples of the anti-APOA2 antibody used in the present invention include anti-APOA2 terminus antibodies (including the anti-APOA2-ATQ terminus antibody and the anti-APOA2-AT terminus antibody) and anti-APOA2 non-terminus antibodies. Each of the antibodies will be described below.

(1) Anti-APOA2-ATQ Terminus Antibody

The term "anti-APOA2-ATQ terminus antibody" represents one of the anti-APOA2 terminus antibodies and refers to an antibody or a fragment thereof that can specifically recognize and bind to an epitope located in the C-terminal region of the APOA2-ATQ protein.

In this specification, the term "C-terminal region (carboxyl-terminal region)" refers to a region in an amino acid sequence, the region comprising the C-terminal amino acid and nearby several consecutive amino acids, in total, 6 to 25 amino acids, preferably 8 to 20 amino acids or 10 to 17 amino acids.

In this specification, by the phrase "specifically recognize and bind to" is meant no or very low cross-reactivity with other APOA2 protein variants, which results in that the antibody cannot recognize and bind to or hardly binds to other APOA2 protein variants. Specifically, the term refers to an antibody that specifically binds to the C-terminal region of the APOA2-ATQ protein but not to the C-terminal regions of the APOA2-AT protein and APOA2-A protein.

(2) Anti-APOA2-AT Terminus Antibody

The term "anti-APOA2-AT terminus antibody" represents one of the anti-APOA2 terminus antibodies and refers to an antibody or a fragment thereof that can specifically recognize and bind to an epitope located in the C-terminal region of the APOA2-AT protein. Specifically, the term refers to an antibody that specifically binds to the C-terminal region of the APOA2-AT protein but not to the C-terminal regions of the APOA2-ATQ protein and APOA2-A protein.

(3) Anti-APOA2 Non-Terminus Antibody

The term "anti-APOA2 non-terminus antibody" refers to an anti-APOA2 antibody that recognizes and binds to an epitope located in the region in the full-length amino acid sequence of an APOA2 protein variant, excluding the C-terminal region as described above. It means that the anti-APOA2 non-terminus antibodies and the anti-APOA2-ATQ or anti-APO2A-AT terminus antibody individually recognize completely different epitopes.

Additionally, the term anti-APOA2 non-terminus antibody includes the word "non-terminus antibody" and is conveniently named for the comparison with the anti-APOA2 terminus antibody. Thus, antibodies that recognize an epitope not localized in the C-terminal region can be included, without limitation, in the anti-APOA2 non-terminus antibodies, even if they recognize and bind to an epitope located at the N-terminus.

The anti-APOA2 non-terminus antibodies used in the present invention are preferably antibodies which have a nearly equivalent level of binding activity when binding activity is compared between an APOA2 protein having a certain C-terminal sequence and another APOA2 protein having a C-terminal sequence different from that of the former APOA2 protein and which do not prevent the binding of the anti-APOA2 terminus antibodies to the C-terminal region. That is, preferably, the anti-APOA2 non-terminus antibodies used in the present invention are not specific for certain variants. Specifically, for example, an "anti-APOA2-ATQ non-terminus antibody" which binds to the amino acid sequence of the APOA2-ATQ protein consisting of the amino acid sequence represented by SEQ ID NO: 1 excluding its C-terminal region and an "anti-APOA2-AT non-terminus antibody" which binds to the amino acid sequence of the APOA2-AT protein consisting of the amino acid sequence represented by SEQ ID NO: 2 excluding its C-terminal region have comparable binding activity to the APOA2 protein and, either antibody does not prevent the anti-APOA2-ATQ terminus antibody and the anti-APOA2-AT terminus antibody from binding to the C-terminal region of the APOA2 protein.

2-2. Type of Antibodies (1) Monoclonal Antibody

The anti-APOA2-ATQ terminus antibody, the anti-APOA2-AT terminus antibody, and the anti-APOA2 non-terminus antibodies may be either polyclonal or monoclonal antibodies, or fragments thereof. Monoclonal antibodies are preferable to enable large-scale production and to achieve a uniform effect.

The term "monoclonal antibody" as used herein refers to an antibody composed of an immunoglobulin, or an antibody that comprises the framework regions (hereinafter referred to as "FRs") and complementarity determining regions (hereinafter referred to as "CDRs") of an immunoglobulin and can specifically recognize and bind to a particular antigen (epitope).

Each typical immunoglobulin molecule is composed as a tetramer comprising two sets of polypeptide pairs linked by disulfide bonds, each pair consisting of two polypeptide chains called heavy and light chains. A heavy chain comprises an N-terminal heavy chain variable region (H chain V region: hereinafter referred to as "VH") and a C-terminal heavy chain constant region (H chain C region: hereinafter referred to as "CH"), while a light chain comprises an N-terminal light chain variable region (L chain V region: hereinafter referred to as "VL") and a C-terminal light chain constant region (L chain C region: hereinafter referred to as "CL"). Among them, VH and VL are particularly important because of their involvement in determining the binding specificity of an antibody. Each of the VH and VL comprises about 110 amino acid residues and has three CDRs (CDR1, CDR2, CDR3), which are directly involved in the determining the binding specificity to the antigen, and four FRs (FR1, FR2, FR3, FR4), which function as a scaffold. It is understood that the CDRs of an antibody form a tertiary structure complementary to an antigen and determine the specificity of the antibody (E. A. Kabat et al., 1991, Sequences of proteins of immunological interest, Vol. 1, 5th ed., NIH publication). The amino acid sequence of the constant region is substantially identical among antibodies from the same species, whereas the amino acid sequences of the CDRs are highly variable among antibodies, thus called "hypervariable regions". In the variable region, CDRs and FRs as described above are arranged from N-terminus to C-terminus in the following order: FR1, CDR1, FR2, CDR2, FR3, CDR3, FR4. In an immunoglobulin molecule, the VL and VH are paired to form a dimer and thereby form an antigen binding site. Immunoglobulin classes of IgG, IgM, IgA, IgE and IgD are known. The antibodies used in the present invention may be of any of the classes and is preferably of the IgG class.

The anti-APOA2-ATQ terminus antibody used in the present invention specifically binds to the C-terminal region of the APOA2-ATQ protein consisting of the amino acid sequence represented by SEQ ID NO: 1 but not to the APOA2-AT protein consisting of the amino acid sequence represented by SEQ ID NO: 2. Specific examples of such an antibody include anti-APOA2-ATQ terminus monoclonal antibody clones, for example, as described in Example 1 below and represented by the antibody clone names "7F2" and "6G2," and the like. The 7F2 clone comprises, in the heavy chain, a CDR1 having the amino acid sequence represented by SEQ ID NO: 3, a CDR2 having the amino acid sequence represented by SEQ ID NO: 4 and a CDR3 having the amino acid sequence represented by SEQ ID NO: 5 and, in the light chain, a CDR1 having the amino acid sequence represented by SEQ ID NO: 6, a CDR2 having the amino acid sequence represented by SEQ ID NO: 7 and a CDR3 having the amino acid sequence represented by SEQ ID NO: 8. Moreover, the 6G2 clone comprises, in the heavy chain, a CDR1 having the amino acid sequence represented by SEQ ID NO: 9, a CDR2 having the amino acid sequence represented by SEQ ID NO: 10 and a CDR3 having the amino acid sequence represented by SEQ ID NO: 11 and, in the light chain, a CDR1 having the amino acid sequence represented by SEQ ID NO: 12, a CDR2 having the amino acid sequence represented by SEQ ID NO: 13 and a CDR3 having the amino acid sequence represented by SEQ ID NO: 14. Examples of such an antibody may include additionally anti-APOA2-ATQ terminus polyclonal antibodies having a similar binding activity. Commercially available antibodies can be used as an anti-APOA2-ATQ terminus antibody.

The anti-APOA2-AT terminus antibody used in the present invention specifically binds to the C-terminal region of the APOA2-AT protein consisting of the amino acid sequence represented by SEQ ID NO: 2 but not to the APOA2-ATQ protein consisting of the amino acid sequence represented by SEQ ID NO: 1. Examples of such an antibody include the anti-APOA2-AT terminus polyclonal antibody used in Examples described below and an anti-APOA2-AT terminus monoclonal antibody having a binding activity similar to that of the polyclonal antibody. Commercially available antibodies can be used as an anti-APOA2-AT terminus antibody.

The anti-APOA2 non-terminus antibodies used in the present invention are preferably antibodies having the same binding activity to the APOA2 protein variant consisting of the amino acid sequence represented by SEQ ID NO: 1 or 2 (i.e., the APOA2-ATQ protein and the APOA2-AT protein) when they are compared for the binding activity to the protein variants. Specific examples include anti-APOA2 monoclonal antibody clones as represented by the antibody clone names "MAB1" and "MAB2," and the like. The MAB1 clone comprises, in the heavy chain, a CDR1 having the amino acid sequence represented by SEQ ID NO: 15, a CDR2 having the amino acid sequence represented by SEQ ID NO: 16 and a CDR3 having the amino acid sequence represented by SEQ ID NO: 17 and, in the light chain, a CDR1 having the amino acid sequence represented by SEQ ID NO: 18, a CDR2 having the amino acid sequence represented by SEQ ID NO: 19 and a CDR3 having the amino acid sequence represented by SEQ ID NO: 20. Moreover, the MAB2 clone comprises, in the heavy chain, a CDR1 having the amino acid sequence represented by SEQ ID NO: 21, a CDR2 having the amino acid sequence represented by SEQ ID NO: 22 and a CDR3 having the amino acid sequence represented by SEQ ID NO: 23 and, in the light chain, a CDR1 having the amino acid sequence represented by SEQ ID NO: 24, a CDR2 having the amino acid sequence represented by SEQ ID NO: 25 and a CDR3 having the amino acid sequence represented by SEQ ID NO: 26. Examples of such antibodies include additionally the anti-APOA2 non-terminus polyclonal antibody used in Examples described below. Commercially available antibodies can be used as an anti-APOA2 non-terminus antibody.

(2) Antibody Fragment

By the term "a fragment thereof" in the phrase "a polyclonal or monoclonal antibody, or a fragment thereof" is meant a partial fragment (an antibody fragment) of a polyclonal or monoclonal antibody, the fragment forming a polypeptide chain or a complex thereof that has an activity substantially comparable to the antigen-specific binding activity owned by the above antibody. For example, the term refers to an antibody portion containing at least one antigen binding site, namely, a polypeptide chain having at least one set of VL and VH, or a complex thereof. Specific examples include a number of well characterized antibody fragments produced by cleavage of immunoglobulins with various peptidases and the like. More specific examples include Fab, F(ab')$_2$, Fab', and the like. Fab is a fragment generated by cleavage of an IgG molecule with papain at a site N-terminal to the disulfide bonds in the hinge region and each fragment is composed of a polypeptide carrying a VH and a CH1, one of the three domains constituting a CH (CH1, CH2 and CH3) located next to the VH, and a light chain. F(ab')$_2$ is a Fab' dimer generated by cleavage of an IgG molecule at a site C-terminal to the disulfide bonds in the hinge region. Fab' has a structure substantially identical to that of Fab, having a slightly longer H chain because of the inclusion of the hinge region (Fundamental Immunology (3rd ed.), Paul ed., 1993). Fab' can be obtained by reducing F(ab')$_2$ under mild conditions to cleave the disulfide linkage in the hinge region. Each of these antibody fragments contains an antigen binding site(s) and has an ability to specifically bind to an antigen (that is, in this specification, a certain variant of the APOA2 protein). Furthermore, the antibody fragments of the present invention include antibody fragments identified using a phage display library (see, for example, McCafferty et al., 1990, Nature, 348: 552-554) and having antigen-binding ability. See also additionally, for example, Kuby, J., Immunology (3rd ed.), 1998, W. H. Freeman & Co., New York.

(3) Synthetic Antibody

The antibodies used in the present invention may be antibodies synthesized chemically or by using recombinant DNA techniques. Examples include synthetic antibodies newly synthesized by using recombinant DNA techniques. Specifically, the term refers to, but not limited to, a polypeptide molecule in monomeric form, which is composed of one or more VLs and one or more VHs of a monoclonal antibody used in the present invention artificially connected with a linker peptide and the like having an appropriate length and sequence, or the polypeptide in multimeric form. Examples of such polypeptides include single-chain Fv (ScFv: single chain Fragment of variable region) (see Pierce catalog and Handbook, 1994-1995, Pierce Chemical Co., Rockford, Ill.), diabody, triabody or tetrabody, etc. In an immunoglobulin molecule, the VL and VH are typically located on separate polypeptide chains (L chain and H chain). A single-chain Fv is a synthetic antibody having a structure with a VL and a VH connected by a flexible linker of sufficient length and thereby including these variable regions in a single polypeptide chain. In a single-chain Fv, both variable regions can undergo self-assembly by mutual association to form one functional antigen binding site. A single-chain Fv can be obtained by expression of a recombinant DNA coding therefor, which has been integrated into the phage genome or a vector such as plasmid and the like by using known technologies. Diabody is a synthetic antibody having an architecture based on the structure of single-chain Fv in dimeric form (Holliger et al., 1993, Proc. Natl. Acad. Sci. USA, 90: 6444-6448). For example, in cases where the length of the above-described linker is shorter than about 12 amino acid residues, the two variable regions in a single-chain Fv cannot undergo self-assembly in the context of conformational structure and then cannot form a functional antigen binding site. However, the formation of a diabody, that is, the interaction between two single-chain Fvs enables the VL on one Fv chain to assemble with the VH on the other Fv chain, leading to the formation of two functional antigen binding sites in total (Marvin et al., 2005, Acta Pharmacol. Sin., 26: 649-658). Furthermore, the addition of a cysteine residue to the C-terminus in two single-chain Fvs can result in the formation of a disulfide bond between the Fv chains, leading to the formation of a stable diabody (Alafsen et al., 2004, Prot. Engr. Des. Sel., 17: 21-27). Although diabody is a bivalent antibody fragment as described above, there is no need for each antigen binding site to associate with the same epitope but may have dual specificity that allows each antigen binding site to recognize and specifically bind to a different epitope. Analogously to diabody, triabody and tetrabody have the trimeric and tetrameric structures based on the single-chain Fv structure, respectively, and are trivalent and tetravalent antibody fragments, respectively, and may be multispecific antibodies.

(4) Modified Antibody

The anti-APOA2 antibodies used in the present invention or fragments thereof may be modified. The modification here includes both functional modification required for the anti-APOA2 antibodies or fragments thereof to have the binding activity specific for the APOA2 protein (for example, glycosylation) and modification for labeling required for the antibodies of the present invention or fragments thereof to be detected. Examples of the labeling of antibodies include labeling with a fluorescent dye (FITC, rhodamine, Texas red, Cy3, Cy5), a fluorescent protein (for example, PE, APC, GFP), an enzyme (for example, horseradish peroxidase, alkaline phosphatase, glucose oxidase), or either biotin or (strept)avidin. Moreover, the glycosylation of antibodies may be modified to adjust the affinity of the antibodies for their antigens. Such modification can be achieved by, for example, altering one or more glycosylation sites within the sequence of an antibody. More specifically, for example, one or more amino acid substitutions can be introduced into an amino acid sequence comprising one or more glycosylation sites within FR to remove the above glycosylation sites and consequently eliminate the glycosylation at those sites. Such deglycosylation is effective to increase the affinity of an antibody to its antigen (U.S. Pat. Nos. 5,714,350 and 6,350,861).

2-3. Production of Anti-APOA2 Antibodies
2-3-1. Preparation of Immunogen

When the anti-APOA2 antibodies used in the present invention are produced, an APOA2 protein or a fragment thereof as an immunogen (an antigen) is first prepared.

(Production of Immunogens for the Anti-APOA2 Terminus Antibodies)

When the anti-APOA2 terminus antibodies are produced, each of the APOA2 protein variants is required as an immunogen.

An APOA2 protein variant for use as an antigen is not particularly limited, as long as it comprises an amino acid sequence comprising 6 or more consecutive amino acids of the C-terminal region in a APOA2 protein having the amino acid sequence represented by either SEQ ID NO: 1 or SEQ ID NO: 2. For example, any APOA2 protein-derived variant selected from naturally-occurring APOA2 proteins, recombinant APOA2 proteins, or synthetic APOA2 proteins may be used. APOA2 protein variants can be synthesized using the amino acid sequence information of SEQ ID NO: 1 or 2 by a procedure known in the art, such as solid-phase peptide synthesis. For example, the preparation can be performed by the method below.

Naturally-occurring APOA2 proteins can be obtained by recovery from biological samples, including body fluid such as blood (including serum and plasma), or cell culture supernatant using known protein separation and purification techniques, such as gel filtration, ion exchange chromatography, and affinity chromatography.

Recombinant APOA2 proteins can be obtained by expression of the above proteins in microbes, insect cells, or animal cells, into which DNAs encoding the above proteins have been introduced, followed by recovery of the proteins from the above cells using known protein separation and purification techniques. A specific preparation method for recombinant APOA2 proteins will be described below.

Synthetic APOA2 proteins can be obtained, for example, using the published information on the amino acid sequence of the APOA2 protein by a procedure known in the art, such as solid-phase peptide synthesis. These synthetic APOA2 proteins may be linked to a carrier protein such as KLH (keyhole limpet hemocyanin), OVA (ovalbumin), or BSA (bovine serum albumin).

Any fragment selected from fragments of naturally-occurring APOA2 proteins, fragments of recombinant APOA2 proteins, or fragments of synthetic APOA2 proteins may likewise be used when a fragment of an APOA2 protein variant is used as an immunogen. For example, with regard to the APOA2 protein fragment, an oligopeptide or polypeptide comprising 6 or more, preferably 10 or more, preferably 18 or more, more preferably 30 or more consecutive amino acid residues including the C-terminus in the amino acid sequence represented by SEQ ID NO: 1 or 2 can be used as an antigen. For example, a peptide comprising the amino acid sequence represented by SEQ ID NO: 27 or 28 can be used.

In cases where a fragment of a naturally-occurring APOA2 protein is used as an immunogen, purified APOA2 proteins are treated with an appropriate protease, such as trypsin, and then applied to a reverse-phase column for the separation and collection of peaks. Subsequently, the amino acid sequence of a peptide corresponding to each peak is identified with a mass spectrometer. One of the peptides may be used as an immunogen if the peptide comprises a sequence comprising, as a partial sequence, 6 or more consecutive amino acids in the C-terminal region of the APOA2 protein represented by SEQ ID NO: 1 or 2.

In cases where a fragment of a recombinant APOA2 protein is used as an immunogen, a DNA sequence coding for a peptide in the APOA2 protein consisting of the amino acid sequence represented by SEQ ID NO: 1 or 2 is inserted into an expression vector, which peptide consists of a partial sequence comprising 6 or more consecutive amino acids including the C-terminal amino acid residue (C-terminal fragment). Subsequently, the expression vector is introduced into various cells for the expression of the encoded C-terminal fragment. Finally, the C-terminal fragment is extracted from the cells according to routine procedures after the completion of the expression. The obtained C-terminal fragment may be used as an immunogen.

(Production of Immunogens for the Anti-APOA2 Non-Terminus Antibodies)

When the anti-APOA2 non-terminus antibodies are produced, each of the APOA2 protein variants is likewise required as an immunogen. The basic preparation method may be identical to the above-described production method for anti-APOA2 terminus antibodies. However, with regard to the region in the APOA2 protein available as an immunogen, a region different from those employed in the production of anti-APOA2 terminus antibodies is used. It means that the whole or a part of the region of the APOA2 protein, excluding the C-terminal region, may be used as an immunogen. Also in cases where anti-APOA2 non-terminus antibody are produced, an oligopeptide or polypeptide comprising amino acid residues in the region of the APOA2 protein, excluding the C-terminal region, can be used as an antigen. The procedure similar to that used in the production of anti-APOA2 terminus antibodies may be used in the production of anti-APOA2 non-terminus antibodies.

(Preparation of Recombinant APOA2 Proteins)

The preparation of a recombinant APOA2 protein comprising the amino acid sequence represented by SEQ ID NO: 1 or 2 (recombinant APOA2 protein variants) will be described in detail below.

(a) Preparation of Polynucleotides Encoding Recombinant APOA2 Protein Variants

Phages or plasmids capable of autonomous replication in host microbes can be used as vectors for use in the expression of various APOA2 protein variants. Examples of the plasmids include plasmids derived from *E. coli* (pET30a, pGEX6p, pUC118, pUC119, pUC18, pUC19 and the like), plasmids derived from *Bacillus subtilis* (pUB110, pTP5 and the like), plasmids derived from yeasts (YEp13, YEp24, YCp50 and the like), and the like. Moreover, examples of the phages include λphages (λgt1, λZAP and the like). Furthermore, vectors of animal viruses such as vaccinia virus or insect viruses such as baculovirus may also be used.

Examples of a method for inserting a polynucleotide encoding an APOA2 protein variant into the above-described vector include a method involving the cleavage of the above purified polynucleotide with an appropriate restriction enzyme(s), followed by the ligation of the resulting polynucleotide using DNA ligase and the like into a vector cleaved with the corresponding restriction enzyme(s).

(b) Introduction of the APOA2 Protein Variant-Expressing Vector into a Host

Transformants capable of the expression of the APOA2 protein variant (variant-expressing transformants) are obtained by introducing the obtained APOA2 protein variant-expressing vector into a host. The used host is not particularly limited as long as it is a host suitable for the used vector, and can allow APOA2 protein variants to be expressed. For example, bacteria (colibacillus (for example, *Escherichia coli*), hay bacillus (for example, *Bacillus subtilis*) and the like), yeasts, insect cells, animal cells (COS cells, CHO cells (Journal of Immunology, 1998, 160: 3393-3402)) and the like are preferably used. The method to introduce the above-described vectors to the bacteria is not particularly limited as long as the method is a known method for introducing the above vectors into the bacteria. Examples of the method include the heat shock method, a method using calcium ions, electroporation and the like. All of these techniques are known in the art and have been described in various literature. See, for example, Green & Sambrook, 2012, Molecular Cloning: A Laboratory Manual (4th ed.), Cold Spring Harbor Laboratory Press, Cold Spring Harbor, N.Y. Moreover, for the transformation of animal cells, the lipofectin method (PNAS, 1989, 86: 6077; PNAS, 1987, 84: 7413), electroporation, the calcium phosphate method (Virology, 1973, 52: 456-467), the DEAE-dextran method and the like are preferably used.

In cases where a bacterium is used as a host, preferably, the APOA2 protein variant-expressing vector is capable of autonomous replication in the above bacterium and, at the same time, comprises a promoter sequence, a ribosome-binding sequence, an APOA2 protein variant-coding DNA sequence and a transcription termination sequence. Moreover, the expression vector may comprise a gene coding for a regulator that controls the promoter. Any promoter may be used as long as it is functional in a host such as *E. coli*.

Also in cases where a eukaryotic cell, such as yeast, animal cells, insect cells and the like, is used as a host, APOA2 protein variant-expressing transformants can likewise be obtained by following a procedure known in the art. The APOA2 protein variant-expressing vector used in eukaryotic cells may be linked with, in addition to a promoter sequence and an APOA2 protein variant-coding DNA sequence, a cis-element such as enhancer, splicing signals (signals for donor site, acceptor site, branch point and the like), a polyadenylation signal, a selection marker sequence, a ribosome-binding sequence (SD sequence) and the like, as required.

(c) Culture of the Variant-Expressing Transformant and Expression of the Recombinant APOA2 Protein Variant Subsequently, the variant-expressing transformant produced above is cultured. The method to culture the variant-expressing transformant is carried out according to a culture method conventionally used for the host. For example, in cases where a bacterium is used as a host, the type of culture medium is not particularly limited as long as the medium contains a carbon source, nitrogen source, inorganic salts and the like, which can be assimilated by the bacterium, and allows the bacterium to grow and proliferate. Either a natural or synthetic medium can be used. More specific examples include, but of course not limited to, the LB medium. Moreover, for the selective culture of the variant-expressing transformant, an antibiotic such as ampicillin or tetracycline may be added as necessary to the culture medium. The culture is usually maintained at 37° C. for 6 to 24 hours under aerobic conditions, for example, with continuous aeration and stirring. During the culture period, the pH is preferably maintained around neutral. The pH is adjusted with an inorganic or organic acid solution, an alkaline solution and the like. In cases where the variant-expressing transformant is based on animal cells such as CHO cell, the host cells may be inoculated in DMEM medium manufactured by Thermo Fisher Scientific, Inc. to a density of $1 \times 10^5$ cells/mL and cultured in an incubator at 37° C. and 5% $CO_2$. During the culture, an antibiotic such as ampicillin or tetracycline may be added as necessary to the culture medium.

In cases where the above-described APOA2 protein variant-expressing vectors are in the form of an inducible protein expression vector comprising a regulatory system for protein expression (corresponding to, in the case of a bacterial host, a repressor gene, an operator and the like, for example), a predetermined treatment should be performed on the variant-expressing transformants to induce the expression of the APOA2 protein variant. Since the method to induce the expression is different depending on the regulatory system for protein expression contained in each vector, an induction treatment suitable for each system may appropriately be performed. For example, a system comprising the lac repressor gene and the lac operator is the regulatory system for protein expression most commonly used in inducible protein expression vectors for bacterial hosts. With this system, expression can be induced by the treatment with IPTG (isopropyl-1-tio-β-D-galactoside). In transformants harboring an APOA2 protein expression vector that comprises this system, it is sufficient for the expression of a protein of interest, the APOA2 protein variant, to add an adequate amount of IPTG (for example, a final concentration of 1 mM) to the culture medium.

(d) Extraction and/or Recovery of the Recombinant APOA2 Protein Variant

In cases where the APOA2 protein variant is produced and stored in bacterial bodies or cells, the protein of interest can be extracted by recovering and breaking the bacterial bodies or cells after the completion of the culture. Moreover, in cases where the APOA2 protein variant is produced and stored outside of bacterial bodies or cells, the culture liquid may be used directly, or the supernatant may be used after the removal of the bacterial bodies or the cells by centrifugation and the like. Subsequently, the APOA2 protein variant can be isolated and purified from the culture using conventional protein purification methods, either individually or in appropriate combinations, such as ammonium sulfate precipitation, gel filtration, ion exchange chromatography, affinity chromatography and the like. It may be confirmed by SDS-polyacrylamide gel electrophoresis and the like whether or not the APOA2 protein variant has been obtained.

2-3-2. Production Methods for Anti-APOA2 Monoclonal Antibodies and Hybridomas

The anti-APOA2 monoclonal antibodies used in the present invention and hybridomas that produce those monoclonal antibodies can be produced by the method described below. However, the production method is not limited to that method and they can also be produced by any other methods known in the art.

(1) Immunization of Mammals with an Immunogen

The immunogen obtained in the above section 2-3-1 is dissolved in a buffer to prepare an immunogen solution. On this occasion, an adjuvant may be added, if necessary, to the buffer for effective immunization. Examples of the adjuvant include commercially available Freund's complete adjuvant (FCA), Freund's incomplete adjuvant (FIA) and the like. These adjuvants may be used individually or in combination.

Next, the prepared immunogen solution is administered to a mammal, such as rat, mouse (for example, BALB/c inbred mouse), rabbit and the like, for immunization. Examples of a method for administrating the immunogen include, but not limited to, subcutaneous injection using FIA or FCA, intraperitoneal injection using FIA, or intravenous injection using 0.15 moles of sodium chloride. A single dose of the immunogen is appropriately determined depending on the species of an animal to be immunized, administration route and the like and is in the range of about 50 to 200 μg per animal. Moreover, the interval between immunizations is not particularly limited, but booster immunization is given 2 to 6 times, preferably 3 to 4 times, with an interval of several days to several weeks, preferably 1 to 4 weeks, after the initial immunization. From the initial immunization, the immunized animal will be measured for the antibody titer in serum by ELISA (Enzyme-Linked Immunosorbent Assay) and the like. Upon the indication of an adequate increase in antibody titer, the immunogen is injected intravenously or intraperitoneally as a final immunization. Subsequently, antibody-producing cells are collected 2 to 5 days, preferably 3 days, after the final immunization.

(2) Recovery of Antibody-Producing Cells from Immunized Animals and Cell Fusion

Hybridomas producing monoclonal antibodies that specifically recognize particular regions of the APOA2 protein can be produced through the cell fusion between antibody-producing cells obtained from the immunized animals and myeloma cells. Examples of the antibody-producing cells include spleen cells, local lymph node cells, peripheral blood cells and the like, and spleen cells or local lymph node cells are preferable. Cells of a commonly available established cell line derived from mouse or the like can be used as myeloma cells to be fused with antibody-producing cells. The cell line to be used preferably has the following characteristics: being selectable by a drug, inviable in an unfused form in the HAT selection medium (containing hypoxanthine, aminopterin and thymine), and viable only in a fused form with antibody-producing cell in the same medium. Moreover, the established cell line is preferably derived from the same species or strain of animals as the immunized animals. Specific examples of myeloma cells include cells of cell lines derived from BALB/c mouse and deficient in hypoxanthine guanine phosphoribosyltransferase (HGPRT), such as the strain P3X62-Ag.8 (ATCC TIB9), P3X63-Ag.8.U1 (JCRB9085), P3/NS1/1-Ag4-1 (JCRB0009), P3x63Ag8.653 (JCRB0028), or SP2/0-Ag14 (JCRB0029).

For the cell fusion between the above-described myeloma cells and antibody-producing cells, in a serum-free medium for animal cell culture, such as the DMEM or RPMI 1640 medium, the antibody-producing cells and the myeloma cells are mixed at a ratio of about 1:1 to 20:1 and undergo a fusion reaction in the presence of a cell fusion promoter. Polyethylene glycol having an average molecular weight of 1,500 to 4,000 Da and the like can be used as a cell fusion promoter at a concentration of about 10 to 80%. Moreover, if necessary, an auxiliary agent such as dimethyl sulfoxide may be used in combination therewith to increase the efficiency of fusion. Furthermore, the antibody-producing cells and the myeloma cells can also be fused with each other using a commercially available cell fusion apparatus that employs electric stimulation (for example, electroporation) (Nature, 1977, 266: 550-552).

(3) Selection of Hybridomas of Interest

In a method for selecting hybridomas that produce the anti-APOA2 monoclonal antibodies of interest from the cells after the cell fusion process, the cell suspension is diluted with, for example, RPMI 1640 and the like containing fetal bovine serum and then seeded at approximately $2 \times 10^6$ cells/well in 96-well microtiter plates. Then, a selection medium is added to each well and the culture is maintained hereafter by changing the selection medium as necessary. The culture temperature is a temperature of 20 to 40° C., preferably about 37° C. In cases where the myeloma cells are of a HGPRT-deficient or thymidine kinase (TK)-deficient line, the use of the selection medium containing hypoxanthine, aminopterin and thymidine (HAT medium) can selectively allow only hybridomas between the antibody-producing cells and the myeloma cells to grow and proliferate. Therefore, cells that have started their growth on the selection medium from approximately 10 days after the initiation of culture may be selected as hybridomas.

The hybridomas selected with the HAT medium are first screened based on the binding activity to various APOA2 protein variants comprising the amino acid sequence represented by SEQ ID NO: 1 or 2. Next, the cross-reactivity is examined for hybridomas producing antibodies that have binding activity to the APOA2 protein variants, and acceptable hybridomas are chosen. The term "acceptable cross-reactivity" means a negligible level of cross-reactivity in applications of the antibodies of interest. For example, in the case of a monoclonal antibody for use in immunological measurement, the monoclonal antibody is considered to undergo practically no cross-reaction when the signal intensity for the cross reaction is kept in the range from the background level to a level of less than 1% of the signal intensity arising from a specific reaction.

The reaction specificity for a particular APOA2 protein variant can be confirmed, for example, using ELISA. In ELISA, various APOA2 protein variants or fragments thereof are provided as antigens individually immobilized on different wells of a microplate and are allowed to react by addition of samples of appropriately diluted culture supernatants of the above-described hybridomas. After sufficient reaction, the wells are washed and further allowed to react by addition of a labeled secondary antibody against an immunoglobulin. The wells are washed again and then assayed using the label of the secondary antibodies remaining bound to the wells in the end. Thus, the binding activity of an antibody present in each culture supernatant for each antigen can be quantitatively defined.

For example, for the purpose of obtaining an anti-APOA2 terminus monoclonal antibody that specifically binds to, among other amino acid sequences constituting APOA2 proteins, the C-terminal region of the APOA2 protein consisting of the amino acid sequence represented by either SEQ ID NO: 1 or SEQ ID NO: 2, an antibody that binds to the particular APOA2 protein variant alone may be screened using an intact APOA2 protein consisting of the amino acid sequence represented by SEQ ID NO: 1 or 2 or a peptide comprising the C-terminal region of the APOA2 protein variant, and an APOA2 protein consisting of an amino acid sequence, excluding the amino acid sequence of SEQ ID NO: 1 or 2 (for example, the APOA2-A protein).

For example, an anti-APOA2-ATQ terminus monoclonal antibody specifically binds to the C-terminal region of the APOA2-ATQ protein consisting of the amino acid sequence represented by SEQ ID NO: 1 but not or hardly to the APOA2-AT protein consisting of the amino acid sequence represented by SEQ ID NO: 2 and a protein generated by the deletion of the C-terminal amino acid from the APOA2-AT protein, i.e., the APOA2-A protein. Thus, an anti-APOA2-ATQ terminus monoclonal antibody can be screened on the basis of the above-described property.

Moreover, an anti-APOA2-AT terminus monoclonal antibody specifically binds to the C-terminal region of the APOA2-AT protein consisting of the amino acid sequence represented by SEQ ID NO: 2 but not or hardly to the APOA2-ATQ protein consisting of the amino acid sequence represented by SEQ ID NO: 1 and a protein generated by the deletion of the C-terminal amino acid from the APOA2-AT protein, i.e., the APOA2-A protein. Thus, an anti-APOA2-AT terminus monoclonal antibody can be screened on the basis of the above-described property.

Furthermore, anti-APOA2 non-terminus antibodies that recognize the amino acids of the APOA2 protein excluding the C-terminal region can be obtained by screening antibodies on the basis of a similar level of binding activity when compared between the binding activity to the APOA2 protein variants represented by either SEQ ID NO: 1 or SEQ ID NO: 2 or to peptides thereof having a different C-terminus.

Hybridomas can also be selected using recombinant DNA techniques. First, mRNA is extracted from a population of hybridomas obtained according to the aforementioned method. A method known in the art may be used for the extraction of mRNA. Subsequently, cDNA copies are obtained from the mRNA using an oligo-dT primer or random primer. PCR is performed using the cDNA as a template and a set of primers, one comprising the base sequence of the signal sequence upstream of a variable region-coding gene and the other comprising a base sequence on the constant region side. Cloning of the obtained amplicons in an appropriate cloning vector can yield a library of the variable region genes of the antibodies produced by the hybridomas. By way of a more specific example, without limitation, PCR is performed using Mouse Ig Primers provided by Novagen and the amplicons (cDNA copies of mouse immunoglobulin variable region) are inserted for cloning to the Eco RI site of Zero Blunt PCR Topo Vector provided by Thermo Fisher Scientific Inc. and a collection of the obtained vectors can be used as a library of genes coding for the amino acid sequences of variable regions. Next, probes are designed based on the amino acid sequences of the variable regions or CDRs disclosed in the present invention and the above-described library is screened for positive clones with those probes. Thus, hybridomas that produce monoclonal antibodies used in the present invention can be selected.

(4) Use of Hybridomas for Monoclonal Antibody Production

The hybridomas can be used for monoclonal antibody production by ascites induction in mouse. Specifically, mice from which originated the cells as a fusion partner used in the production of the hybridomas, or nude mice are inoculated intraperitoneally with the hybridomas and ascites fluid is collected appropriately and, consequently, the ascites fluid containing monoclonal antibodies can be harvested. More specifically, BALB/c mice are inoculated intraperitoneally with pristane and 10 days later with the hybridomas developed by using SP2/0 cells as a fusion partner and, consequently, the ascites fluid containing monoclonal antibodies can be harvested.

Moreover, the hybridomas can be used for monoclonal antibody production, in which a suitable culture medium is used for the culture of the hybridomas. Specifically, without limitation, the hybridomas are inoculated in the Hybridoma-SFM medium manufactured by Thermo Fisher Scientific, Inc. to a density of $1\times10^5$ cells/mL and cultured in an incubator at 37° C. and 5% $CO_2$ until the hybridomas are killed and, consequently, culture supernatants containing monoclonal antibodies can be obtained.

(5) Method for Producing Recombinant Anti-APOA2 Monoclonal Antibodies or Fragments Thereof by Recombinant DNA Procedures The antibodies or fragments thereof used in the present invention can also be obtained by recombinant DNA procedures using the information on the cDNA sequences coding for the amino acid sequences of those antibodies.

The use of base sequences coding for the amino acid sequences of the variable regions in an antibody derived from an anti-APOA2 monoclonal antibody-producing hybridoma, such as antibodies derived from an anti-APOA2 terminus monoclonal antibody-producing hybridomas obtained by the above-described method, can allow the base sequences of the VH and VL to be linked with the base sequences encoding any CH and CL, respectively, and each of the resulting polynucleotides to be integrated into an appropriate expression vector, introduced into a host cell(s), and then expressed as an intact immunoglobulin molecule. Alternatively, the use of the CDR grafting antibody technique may allow polynucleotides encoding the amino acid sequences of the CDR sequences within the amino acid sequences of the variable regions in an antibody, which is derived from an anti-APOA2 terminus monoclonal antibody-producing hybridoma obtained by the above-described method, to be connected with polynucleotides encoding the amino acid sequences of human FR sequences in a given order, and each of the resulting polynucleotides to be integrated into an appropriate expression vector, introduced into a host cell(s), and then expressed as an intact immunoglobulin molecule. It is convenient for this process to express heavy and light chains in the same host cell and to produce a dimer composed of the heavy and light chains. Specifically, for example, cells can be co-transformed with a light chain expression vector and a heavy chain expression vector to obtain an antibody used in the present invention from those transformed cells. Alternatively, each of the polynucleotides encoding the amino acid sequences of the above-described variable regions can also be directly integrated into an appropriate expression vector, introduced into host cells, and then expressed as fragments of an immunoglobulin molecule. Alternatively, as described above, polynucleotides encoding the VL and VH, or the light chain and heavy chain, comprising the above-described amino acid sequences may be connected via an appropriate linker, integrated in the phage, and then expressed as a single-chain Fv or a synthetic antibody fragment such as diabody. In addition, according to the recently developed phage display antibody technique (Brinkmann et al., 1995, J. Immunol Methods, 182, 41-50; International Publication Nos. WO97/13844 and WO90/02809), which utilizes genetic engineering techniques to express recombinant antibodies on phage surface, diverse single-chain Fv antibodies resulted from artificial shuffling of genes encoding heavy and light chains are expressed as phage fusion proteins and thereby specific antibodies can be obtained.

The preparation of a polynucleotide encoding a recombinant anti-APOA2 antibody or a fragment thereof, the preparation of a vector integrated with the polynucleotide and the introduction of the vector to a host may be carried out using recombinant DNA techniques known in the art. The recombinant anti-APOA2 protein antibody of interest or a fragment thereof can be obtained from the culture media of the transformed cells or from the inside of those cells.

By way of examples of an immunoglobulin expression vectors, plasmids, phagemids, cosmids, virus vectors (for example, SV40 virus-based vectors, EB virus-based vectors, BPV-based vectors) and the like can be used, but not limited thereto. For example, the BCMGS Neo vector, one of the BPV-based vectors, is a desirable vector that efficiently expresses a foreign gene in COST cells and the like upon transformation (Hajime Karasuyama, "Bovine papilloma virus vectors" in Masami Muramatsu and Hiroto Okayama eds., 1991, Experimental Medicine Supplement: Genetic Engineering Handbook, Yodosha Co., Ltd., 297-299).

Each of the above-described vectors can harbor, in addition to a polynucleotide encoding an antibody or a fragment thereof, regulatory elements essential for the expression of the antibody or a fragment thereof (for example, a promoter, an enhancer, a terminator, a polyadenylation site, splicing sites), or, if necessary, a selection marker.

As a host for transformation, in addition to the hosts described above in the section "2-3-1. Preparation of immunogen," the SP2/0 (mouse myeloma) cell (European Journal of Cancer Prevention (1996) 5: 512-519: Cancer Research (1990) 50: 1495-1502) is preferably used.

In host cells according to this specification which harbor a vector that expresses an antibody or a fragment thereof, the antibody can be produced in the culture supernatant or in the host cells by culturing the host cells according to a conventional method. Specifically, in cases where CHO cell is used as a host, the host cells are inoculated in DMEM medium manufactured by Thermo Fisher Scientific, Inc. to a density of $1\times10^5$ cells/mL and cultured in an incubator at 37° C. and 5% $CO_2$ and, consequently, a culture supernatant containing antibodies can be obtained. Alternatively, for example, in cases where the host cell is *E. coli*, the host cells are inoculated in a culture medium commonly used for the culture of *E. coli*, such as the LB medium, cultured and induced for protein expression and, consequently, the antibody can be produced in the culture supernatant or in the host cells.

When the expression product, namely an antibody or a fragment thereof, contains a constant region, the product can be recovered and purified from the culture supernatant or cell lysate by using Protein A column, Protein G column, anti-immunoglobulin antibody affinity column and the like. On the other hand, when the product is composed of a variable region alone and expressed in a form without constant regions, other suitable purification methods are employed because the above-described method is not applicable. For example, if the product is expressed as a fusion with a C-terminal tag sequence advantageous for purification, such as histidine tags, the product can be purified by affinity chromatography using the corresponding ligand. In cases where the product is not a tagged fusion protein, the product can be purified according to conventional methods for protein purification including ammonium sulfate precipitation, ion exchange chromatography, reverse-phase chromatography, gel filtration chromatography, and hydroxyapatite chromatography.

The monoclonal antibodies or fragments thereof used in the present invention are preferably examined in advance of use for cross-reactivity with other variants, as mentioned above, to confirm their specificity for a particular APOA2 protein variant or a fragment thereof. For example, in the anti-APOA2-ATQ terminus monoclonal antibody used in the present invention or a fragment thereof, antigens to be examined for cross-reactivity are the APOA2-AT protein and the APOA2-A protein.

Moreover, the antibodies used in the present invention or fragments thereof are more preferably examined for cross-reactivity with, in addition to the above-described proteins, other proteins that have a partial structure shared with the APOA2 protein variants. For example, ELISA using the APOA2-ATQ protein as an antigen can be employed to check the cross reaction. When another antigen protein to be examined for its cross-reactivity coexists in the reaction of an antibody to be examined for its reaction specificity, namely an anti-APOA2 terminus antibody and a fragment thereof, with the APOA2 protein variant, the cross-reactivity can be examined by observing the competition between both antigens. In such a method to examine cross-reactivity based on the principle of competitive inhibition, a reaction system is not required to be prepared for each antigen and, thus, the screening can be carried out quickly.

2-3-3. Production of Anti-APOA2 Polyclonal Antibodies

An anti-APOA2 polyclonal antibody can be produced by a method known in the art. Immunogen and immunization of mammals may be performed according to the above method described in the section "2-3-2. Production methods for anti-APOA2 monoclonal antibodies and hybridomas". A method for obtaining an anti-APOA2 terminus polyclonal antibody will be described below in such a manner that the differences from the production method for anti-APOA2 monoclonal antibodies are focused.

For the purpose of producing an anti-APOA2 terminus polyclonal antibody, a C-terminal fragment with a length of at least 6 amino acids or more from the sequence of a particular APOA2 protein variant, such as a peptide consisting of the amino acid sequence represented by SEQ ID NO: 27 or 28, is first dissolved in a buffer to prepare an immunogen solution. An adjuvant may be added, if necessary, to the buffer for effective immunization. Examples of the adjuvant include commercially available Freund's complete adjuvant (FCA), Freund's incomplete adjuvant (FIA) and the like. These adjuvants may be used individually or in combination. Next, the prepared immunogen solution is administered to a mammal, such as rat, mice (for example Balb/c inbred mouse), rabbit and the like, for immunization. A single dose of the immunogen solution is appropriately determined depending on the species of an animal to be immunized, administration route and the like and may contain an amount of immunogen in the range of about 50 to 200 μg per animal. Examples of a method for administering the immunogen solution include, but not limited to, subcutaneous injection using FIA or FCA, intraperitoneal injection using FIA, or intravenous injection using 150 mM sodium chloride. Moreover, the interval between immunizations is not particularly limited, but booster immunization is given 2 to 10 times, preferably 3 to 4 times, with an interval of several days to several weeks, preferably 1 to 4 weeks, after the initial immunization. From the initial immunization, the immunized animal will be repeatedly measured for the antibody titer in serum by ELISA (Enzyme-Linked Immuno Sorbent Assay) and the like. Upon the indication of an adequate increase in antibody titer, the immunogen solution is injected intravenously or intraperitoneally as a final immunization. An antiserum containing a polyclonal antibody that recognizes the APOA2 protein can be harvested from the blood after the immunization.

2-3-4. Purification of Anti-APOA2 Antibodies (1) Production of Peptide-Immobilized Column Affinity columns are produced, on which either a peptide corresponding to the C-terminal region of the APOA2 protein or a peptide corresponding to the C-terminal region of the APOA2 protein and modified by the addition of an amide group to the C terminus is immobilized. The detailed method is described in "Experimental Protocols for Anti-Peptide Antibodies," 2nd ed., Gakken Medical Shujunsha Co., Ltd. Examples of carriers used in the affinity columns include carriers, such as formyl-Cellulofine and CNBr agarose, which have functional groups capable of binding to amino groups of peptides, or carriers capable of binding to cysteine residues of peptides in their sequences through the interaction with maleimide groups covalently linked to the carriers, or the like. Moreover, the length of the peptides to be immobilized is 6 or more amino acids, preferably 10 or more amino acids, preferably 18 or more amino acids, and more preferably 30 or more amino acids, as long as those peptide contains the C-terminus of the APOA2 protein.

(2) Purification of Antibody

Anti-APOA2 antibodies can be purified using the peptide-immobilized affinity columns from the above-described ascites fluid, cell culture supernatant, or antiserum. For example, the antiserum is diluted with a suitable buffer, IgG antibodies contained in the diluted antiserum are allowed to be adsorbed to the affinity column containing the immobilized peptide which corresponds to the C-terminal region of the APOA2 protein, and then the adsorbed fraction is recovered. Subsequently, the affinity column containing the immobilized C-terminally amidated peptide of the APOA2 protein is used to remove immunoglobulins which have binding activity to the peptide excluding the C-terminal region through their adsorption onto the column. Finally, the unadsorbed fraction is obtained as an anti-APOA2 antibody that specifically recognizes a particular APOA2 protein variant.

3. Detection Method for Pancreatic Exocrine Dysfunction

An aspect of the present invention relates to a method for detecting pancreatic exocrine dysfunction in vitro. The present invention is characterized by measuring the amount of APOA2-ATQ protein or APOA2-AT protein present in body fluid of a test subject and determining the presence or absence of pancreatic exocrine dysfunction in the subject on the basis of the measured amount.

The method of the present invention comprises (1) a process of measuring markers for the detection of pancreatic exocrine dysfunction and (2) a process of determining pancreatic exocrine dysfunction. Those steps are described in detail below.

3-1. Process of Measuring Markers for the Detection of Pancreatic Exocrine Dysfunction The "process of measuring markers for the detection of pancreatic exocrine dysfunction" is a process of measuring in vitro the quantity of markers for the detection of pancreatic exocrine dysfunction according to the present invention, namely the amount of the APOA2-ATQ protein or the APOA2-AT protein, or fragments thereof, present in a body fluid derived from a test subject.

In this specification, the term "body fluid" refers to a sample provided for the detection of pancreatic exocrine dysfunction and means biological fluid. The body fluid is not particularly limited but may be a biological fluid that potentially contains the markers used in the present invention for detecting pancreatic exocrine dysfunction. Examples of the body fluid include blood, urine, lymphocyte culture supernatant, cerebrospinal fluid, digestive juice (including, for example, pancreatic juice, colon fluid, fluids secreted from the esophageal gland, and saliva), sweat, ascites, pleural effusion, synovial fluid, nasal mucus, tear fluid, vaginal secretion, semen and the like. It is preferably blood or urine. In this specification, the term "blood" includes plasma and serum, and whole blood may preferably be used. The type of whole blood is not limited, but includes venous blood, arterial blood, cord blood and the like. The body fluid may be a combination of two or more different fluids obtainable from the same individual. The method of the present invention for detecting pancreatic exocrine dysfunction permits the detection even in a low invasive blood or urine sample and, therefore, considered to be very useful as a convenient detection method.

The phrase "body fluid derived from a test subject" refers to a body fluid collected from a test subject. A body fluid derived from a test subject may be applied to the method of the present invention immediately after the collection from the test subject. Alternatively, the body fluid refrigerated or frozen after the collection, directly or with an appropriate treatment, may be brought back to room temperature before application and then applied to the method of the present invention. The appropriate treatment before refrigeration or freezing include, for example, in cases where the body fluid is blood, anticoagulation treatment by the addition of heparin and the like to the collected whole blood, followed by separation into plasma or serum, and the like. These treatments may be performed based on techniques known in the art.

In this specification, the phrase "the amounts of APOA2 protein variants" refers to the quantity of either of the above-described two APOA2 protein variants present in a body fluid derived from a test subject. The quantity may be expressed as absolute or relative. When the quantity represents an absolute amount, it corresponds to the mass or capacity of either of the two APOA2 protein variants contained in a given volume of body fluid. When the quantity represents a relative amount, it refers to, for example based on the use of a standard reference substance, a relative value determined by comparing the measured value of either of the two APOA2 protein variants derived from a test subject to the measured value of the standard reference substance. Examples of the relative amount include concentration, fluorescence intensity, absorbance and the like.

The amounts of the APOA2 protein variants can be measured in vitro using a known method. Examples of the method include a method in which substances capable of specific binding to either of the two APOA2 protein variants, that is, APOA2 terminus-binding molecules are used for measurement. Examples of the APOA2 terminus-binding molecule include an APOA2-ATQ terminus-binding molecule capable of specific binding to the C-terminal region of APOA2-ATQ and an APOA2-AT terminus-binding molecule capable of specific binding to the C-terminal region of APOA2-AT.

In this specification, the phrase "capable of specific binding to" means that a certain substance can substantially bind to a particular APOA2 protein variant, that is, a target of the present invention alone. In this case, non-specific binding may be present at such a level that the detection of a particular APOA2 protein variant is not influenced.

Examples of the "APOA2 terminus-binding molecule" include APOA2-binding proteins and APOA2-binding nucleic acids.

Examples of the "APOA2-binding protein" include anti-APOA2 antibodies. More specifically, the term represents "anti-APOA2 terminus antibodies" raised against APOA2 protein variants as antigens and recognizing the difference in structure among the C-terminal regions of and binding to the APOA2 protein variants, preferably "anti-human APOA2 terminus antibodies" each raised against a human APOA2 protein variant comprising the amino acid sequence of SEQ ID NO: 1 or 2 as an antigen and recognizing and binding to any one of the APOA2 protein variants alone, or antibody fragments thereof. Alternatively, the APOA2-binding proteins may be chemically modified derivatives thereof. The "chemically modified derivatives" here include, for example, both functional modification required for the above anti-APOA2 terminus antibodies or antibody fragments thereof to acquire or retain the binding activity specific for a particular APOA2 protein variant and modification for labeling required for the above anti-APOA2 terminus antibodies or antibody fragments thereof to be detected.

The antibody used for the detection of the APOA2 protein variants may be either polyclonal or monoclonal antibody. Monoclonal antibody is preferable to allow specific detection. For example, an anti-APOA2 terminus polyclonal antibody and the like that specifically bind to the APOA2 terminus can be produced by the aforementioned method.

Examples of the "APOA2-binding nucleic acid" include APOA2 nucleic acid aptamers. The term "nucleic acid aptamer" refers to an aptamer composed of nucleic acid, which is a ligand molecule having an ability to rigidly and specifically associate with its target substance and specifically inhibit or reduce the function, such as physiological activity, of the target substance by virtue of the three-dimensional structure of the single-chain nucleic acid molecule formed on the basis of the secondary and tertiary structures thereof through hydrogen bonding and the like. Specifically, the term represents "APOA2 terminus aptamers" recognizing the difference in structure among the C-terminal regions of and binding to APOA2 protein variants, preferably "human APOA2 terminus aptamers" produced for a human APOA2 protein variant comprising the amino acid sequence of SEQ ID NO: 1 or 2 as a target and recognizing and binding to any one of the APOA2 protein variants alone, or fragments thereof, or alternatively "APOA2 non-terminus aptamers" recognizing and binding to the regions of the APOA2 protein variants, excluding the C-termini.

The nucleic acid aptamers used in this process can be produced by a method known in the art. Examples of the method include an in vitro selection method employing the SELEX (systematic evolution of ligands by exponential enrichment) method. For example, in the case of separation of an RNA aptamer, the SELEX method is a method to select an RNA molecule having a stronger binding activity to its target molecule through repetition of a sequential cycle of the following steps for a total of several to dozens of rounds: RNA molecules associated with a target molecule are selected from an RNA pool composed of a number of RNA molecules each having a random sequence region flanked by primer binding regions; the recovered RNA molecules are amplified by RT-PCR; transcription is performed with the obtained cDNA molecules as templates to obtain amplified products of the selected RNA molecules in a new RNA pool for the next round of reaction. On the other hand, also in the case of separation of a DNA aptamer by the SELEX method, the same basic procedure is used, but recovered DNA molecules are not required to undergo RT-PCR when they are amplified. The base sequences of the random sequence region and the primer binding regions are not particularly limited with regard to length. In general, the random sequence region is preferably in the range of 20 to 80 bases and each primer binding region is preferably in the range of 15 to 40 bases. To increase the specificity for a target molecule, a RNA pool or a DNA pool may be mixed preliminarily with a molecule analogous to the target molecule and, then, a pool composed of RNA molecules or DNA molecules which have not associated with the analogous target molecule may be used. By carrying out the above-described method with the APOA2 protein or an APOA2 protein variant as a target molecule, the finally obtained nucleic acid molecule may be used as an APOA2 nucleic acid aptamer. Additionally, the SELEX method is a known method and may be performed specifically according to, for example, Pan et al., (Proc. Natl. Acad. Sci. U.S.A., 1995, 92: 11509-11513).

It is generally known that RNA aptamers and DNA aptamers are included in nucleic acid aptamers, but the type of the nucleic acid constituting the nucleic acid aptamers according to this specification is not particularly limited. Examples of the aptamers include DNA aptamers, RNA aptamers, aptamers composed of a combination of DNA and RNA, and the like. In general, RNA aptamers are frequently used. However, DNA aptamers are superior in terms of stability, manufacturing cost for chemical synthesis, and the number of steps in the aptamer production.

The nucleic acid aptamers used in this process may be labeled with a labeling substance, such as fluorescent substances (for example, FITC, Texas, Cy3, Cy5, Cy7, Cyanine 3, Cyanine 5, Cyanine 7, FAM, HEX, VIC, fluorescamine and derivatives thereof, and rhodamine and derivatives thereof), radioisotopes (for example, $^{32}P$, $^{33}P$, $^{35}S$), or either biotin or (strept)avidin, to the extent that the labeling does not inhibit the ability of the aptamers to associate with their target molecules.

The two APOA2 protein variants can be measured by an immunological method using anti-APOA2 antibodies individually binding to a particular APOA2 protein variant alone or a binding method using APOA2 terminus aptamers individually binding to a particular APOA2 protein variant alone.

The immunological method may be any method as long as anti-APOA2 antibodies are used, and it is preferably ELISA which is performed using anti-APOA2 terminus antibodies as immobilized or labeled antibodies in combination with another antibody which binds to the region of the APOA2 protein, excluding the C-terminus (anti-APOA2 non-terminus antibody). For example, the amount of the APOA2-ATQ protein can be measured by sandwich ELISA using the anti-APOA2-ATQ terminus antibody as a labeled antibody and the anti-APOA2-ATQ non-terminus antibody as an immobilized antibody. Moreover, the APOA2-AT protein can be measured by sandwich ELISA using the anti-APOA2-AT terminus antibody as an immobilized antibody and the anti-APOA2-AT non-terminus antibody as a labeled antibody. Anti-APOA2 non-terminus antibodies are commercially available from Abcam PLC, Fitzgerald Industries International, and the like, and such commercially available products may be used.

As for the binding method using the APOA2 aptamers, an approach essentially similar to the immunological method may be applied for measurement. Examples of the method include a method in which the APOA2 terminus aptamers are used as immobilized or labeled aptamers in combination with an APOA2 non-terminus aptamer.

3-2. Process of Determining Pancreatic Exocrine Dysfunction

The "process of determining pancreatic exocrine dysfunction" is a process of determining or evaluating in vitro the presence or absence of pancreatic exocrine dysfunction based on the amounts of the proteins measured in the process of measuring the markers for the detection of pancreatic exocrine dysfunction described above. The measured markers for the detection of pancreatic exocrine dysfunction, that is, the amounts of APOA2 protein variants (the amount of the APOA2-ATQ protein or the APOA2-AT protein) in a body fluid sample from a test subject are determined and the presence or absence of pancreatic exocrine dysfunction is determined. According to this determination process, the determination may be made with the amount of either the APOA2-ATQ protein or the APOA2-AT protein alone, while the presence or absence of pancreatic exocrine dysfunction can be determined with higher accuracy by combination of both the amounts. Each step of the determining process will be described in detail below.

The presence or absence of pancreatic exocrine dysfunction can be determined on the basis of the amount of the APOA2-ATQ protein. Specifically, the amount of the APOA2-ATQ protein in a body fluid sample from a test subject is measured using the APOA2-ATQ terminus-binding molecule which specifically binds to the C-terminal region of the APOA2-ATQ protein consisting of the amino acid sequence represented by SEQ ID NO: 1, and an APOA2-ATQ non-terminus-binding molecule which binds to the amino acid sequence excluding the C-terminal region. When the amount of APOA2-ATQ in the body fluid sample from the test subject is smaller than that in healthy subjects, the test subject can be evaluated to have a pancreas affected by pancreatic exocrine dysfunction and, furthermore, the pancreatic exocrine dysfunction can be evaluated as disturbance of pancreatic juice flow.

The presence or absence of pancreatic exocrine dysfunction can be determined on the basis of the amount of the APOA2-AT protein. Specifically, the amount of the APOA2-AT protein is measured using the anti-APOA2-AT terminus antibody which specifically binds to the C-terminal region of the APOA2-AT protein consisting of the amino acid sequence represented by SEQ ID NO: 2, and the anti-APOA2-AT non-terminus antibody which binds to the amino acid sequence excluding the C-terminal region. When the amount of APOA2-AT in the body fluid sample from the test subject is smaller than that in normal subjects, the test subject can be evaluated to have a pancreas affected by pancreatic exocrine dysfunction. Alternatively, when the amount of APOA2-AT in the body fluid sample from the test subject is equal to or more than that in normal subjects, the test subject can be evaluated to have a pancreas at least not affected by insufficient production of pancreatic juice. If the test subject could be evaluated here at least not to have insufficient production of pancreatic juice, it would be useful as the basis for decision to determine the necessity to administer pancreatic enzyme supplements and/or the amounts thereof to be administered.

The presence or absence of pancreatic exocrine dysfunction is detected based on the amount of the APOA2-AT protein alone, as described above, and then the amount of the APOA2-ATQ protein is measured. The results from the respective measurements can be combined to determine which category the pancreatic exocrine dysfunction falls under, disturbance of pancreatic juice flow or insufficient production of pancreatic juice. Specifically, when the amounts of the APOA2-AT protein and the APOA2-ATQ protein in the body fluid sample from the test subject are smaller than those in normal subjects, the pancreatic exocrine dysfunction can be evaluated as disturbance of pancreatic juice flow. On the other hand, when the amount of the APOA2-AT protein in the body fluid sample from the test subject is smaller than that in normal subjects and the amount of the APOA2-ATQ protein is equal to or more than that in normal subjects, the pancreatic exocrine dysfunction can be evaluated as insufficient production of pancreatic juice.

In the present invention, the amounts of the APOA2-AT protein and the APOA2-ATQ protein in a body fluid sample from a test subject can be compared with those in normal subjects by comparing the values of the quantity of the APOA2-AT protein and the quantity of the APOA2-ATQ protein between them.

The respective amounts of the APOA2-ATQ protein and the APOA2-AT protein equal to or more than the corresponding minimum values in a population of normal subjects may be evaluated to be "equal to or more than" those in normal subjects, while the amounts of those proteins less than the corresponding minimum values in the population of normal subjects may be evaluated to be "smaller than" those in normal subjects. Furthermore, when the amounts of those proteins are evaluated to be "smaller than" those in normal subjects, as described above, the respective amounts of the APOA2-ATQ protein and the APOA2-AT protein in a body fluid sample from a test subject are more preferably equal to or less than half of the corresponding minimum values in the population of normal subjects.

In addition to the above-described method, statistical processing can be used when the amount of the APOA2-ATQ protein or the APOA2-AT protein in a test subject is compared with that in normal subjects to determine whether the amount in the former subject is smaller than that in the latter subjects, and only a test subject who has been determined in the analysis to show a statistically significantly "smaller" value than that in the normal subjects can be evaluated to show "a smaller value than that in normal subjects". The phrase "statistically significant" refers to, for example, the case where the error probability (significance level) for an obtained value is small and is specifically at the level of $p<0.05$, $p<0.01$, or $p<0.001$. The term "p" or "p-value" herein refers to the possibility in a statistical test where a hypothesis is true by chance in the context of the hypothesized distribution of statistics. Accordingly, a smaller "p" or "p-value" means that the hypothesis is more likely to be true. The phrase "statistically significantly different" represents here that there is a significant difference between both test and normal subjects when the quantities of the markers for the detection of pancreatic exocrine dysfunction obtained from each of the test subject and the normal subjects are statistically processed. When the test subject is statistically significantly different relative to the normal subjects, the test subject can be evaluated to have pancreatic exocrine dysfunction. A test method for statistical processing is not particularly limited but a known method of test, with which a decision of significance or lack or significance can be made, may be appropriately employed. For example, a Student's test, a multiple-comparison test, or the like may be employed.

The concentrations of the markers for the detection of pancreatic exocrine dysfunction in body fluid from normal subjects may be measured every time the concentrations of the markers for the detection of pancreatic exocrine dysfunction in body fluid from a test subject is measured, or the previously measured concentrations of the markers for the detection of pancreatic exocrine dysfunction may be used. Particularly, it will be convenient to measure in advance the concentrations of the markers for the detection of pancreatic exocrine dysfunction in normal subjects under various physical conditions and to enter those values into a computer for database purpose, because the concentrations of the markers for the detection of pancreatic exocrine dysfunction in a normal subject who has optimal physical conditions for the comparison with a test subject will be readily available once the physical conditions of the test subject are entered into the computer.

4. Detection Kit for Pancreatic Exocrine Dysfunction

A "detection kit for pancreatic exocrine dysfunction" used in the present invention refers to a kit used directly or indirectly to evaluate the presence or absence of pancreatic exocrine dysfunction.

The kit according to the present invention comprises, as its components, APOA2-binding molecules capable of specific binding to APOA2 protein variants, such as anti-APOA2 terminus antibodies and/or APOA2 terminus aptamers. Specifically, antibodies including the anti-APOA2-ATQ terminus antibody, the anti-APOA2-AT terminus antibody, and/or chemically modified derivatives thereof, and/or an APOA2-ATQ terminus aptamer and an APOA2-AT terminus aptamer are included.

Specific examples of the anti-APOA2-ATQ terminus antibody include an anti-APOA2 terminus monoclonal antibody or a fragment thereof which specifically binds to the C-terminal region of the APOA2-ATQ protein consisting of the amino acid sequence represented by SEQ ID NO: 1, wherein the CDR1, CDR2 and CDR3 of the heavy chain are consisting of the amino acid sequences represented by SEQ ID NOs: 3, 4 and 5, or SEQ ID NOs: 9, 10 and 11, respectively, and wherein the CDR1, CDR2 and CDR3 of the light chain are consisting of the amino acid sequences represented by SEQ ID NOs: 6, 7 and 8, or SEQ ID NOs: 12, 13 and 14, respectively.

Furthermore, examples of the component include an anti-APOA2 non-terminus monoclonal antibody or a fragment thereof which recognizes the amino acid sequence of the APOA2-ATQ protein represented by SEQ ID NO: 1 or the APOA2-AT protein consisting of the amino acid sequence represented by SEQ ID NO: 2, excluding the C-terminal region, wherein the CDR1, CDR2 and CDR3 of the heavy chain are consisting of the amino acid sequences represented by SEQ ID NOs: 15, 16 and 17, or SEQ ID NOs: 21, 22 and 23, respectively, and wherein the CDR1, CDR2 and CDR3 of the light chain are consisting of the amino acid sequences represented by SEQ ID NOs: 18, 19 and 20, or SEQ ID NOs: 24, 25 and 26, respectively. One or more monoclonal antibodies, or fragments thereof, selected from these fragments can be used in the detection kit for pancreatic exocrine dysfunction.

The above-described APOA2-binding molecules may be bound to a solid carrier and, in this case, preferably bound to a test strip. In addition, for example, labeled secondary antibodies or labeled probes and, furthermore, substrates required for the detection of the labels, a carrier, a washing buffer, a sample diluting solution, enzyme substrates, a reaction stopping solution, purified APOA2 proteins as the standard reference substances, and an instruction manual and the like may be included.

EXAMPLES

The present invention will be described more specifically by the following Examples. However, the scope of the present invention is not limited by the Examples.

Example 1: Detection of Pancreatic Exocrine Dysfunction by Using the APOA2-ATQ Protein or the APOA2-AT Protein in Blood as a Biomarker
(1)

The relationship between the amounts of the indicated two APOA2 protein variants and the concentration of pancreatic amylase in serum obtained from patients with pancreatic ductal carcinoma was examined.

Serum samples collected with informed consent from 6 patients with pancreatic ductal carcinoma (Samples A to F) and 10 healthy subjects were measured by ELISA for the concentrations of the APOA2-ATQ protein and the APOA2-AT protein to compare the result to the detection method for pancreatic exocrine function based on the concentration of pancreatic amylase.

(Measurement of the Amount of the APOA2-ATQ Protein)

The measurement of the amount of the APOA2-ATQ protein in serum was carried out by sandwich ELISA using a POD-labeled derivative of the anti-APOA2-ATQ terminus monoclonal antibody 7F2 and an anti-APOA2 non-terminus polyclonal antibody which recognizes the region of the APOA2 protein excluding the C-terminal region (Fitzgerald Industries International). The labeling of the antibody 7F2 with POD was carried out using the Peroxidase Labeling Kit-SH and the details of the labeling followed the appended protocol of the kit. An anti-APOA2 non-terminus polyclonal antibody solution in PBS was prepared at a concentration of 2 μg/mL and, then, 100 μL of the solution was dispensed into each well of an Immunoplate MaxiSorp plate (Nunc) for overnight immobilization. Next day, the above solution was discarded, 400 μL of PBS-T (0.05% Tween-20 in PBS) was added to each well for washing, and 400 μL of a blocking buffer solution (1% BSA and 0.05% Tween-20 in PBS) was added to each well and incubated at room temperature for one hour. Subsequently, the above solution was discarded to obtain an antibody-immobilized plate. Next, 100 μL of a plasma sample diluted with a dilution solution was added to each well to allow reaction at room temperature for one hour. In this case, the dilution factor was 10,000. After the antigen solution in each well was discarded, the well was washed with PBS-T and 100 μL of the POD-labeled derivative of the antibody 7F2 diluted with the dilution solution to a concentration of 0.2 μg/mL was added to each well to allow reaction at room temperature for one hour. After washing with PBS-T, 100 μL of TMB solution (manufactured by Pierce) was added to each well for an enzyme reaction, 100 μL of 0.5 N sulfuric acid was added to stop the reaction, and then the absorbance was measured at 450 nm. The concentration of the protein in blood was calculated based on the comparison of the obtained measured value to that from a recombinant human APOA2-ATQ protein antigen solution as a reference standard.

(Measurement of the Amount of the APOA2-AT Protein)

The measurement of the amount of the APOA2-AT protein in serum was carried out in the same serum samples as described above, similarly to the measurement of the amount of the APOA2-ATQ protein described above, by sandwich ELISA using an anti-APOA2-AT terminus polyclonal antibody and a POD-labeled derivative of the anti-APOA2 non-terminus polyclonal antibody. The labeling of the anti-APOA2 non-terminus polyclonal antibody with POD and the sandwich ELISA were performed similarly as described above. The concentration of the protein in blood was calculated based on the comparison of the obtained measured value to that from a recombinant human APOA2-AT protein antigen solution as a reference standard.

(Measurement of the Amount of Pancreatic Amylase)

The measurement of the amount of pancreatic amylase in serum was carried out in the same serum samples as described above by using the Pancreatic Amylase Human ELISA Kit (Abcam PLC). The antibody-immobilized 96-well plate, the washing solution, the biotinylated anti-pancreatic amylase antibody and the POD-streptavidin conjugate, and the pancreatic amylase standard for generating a standard curve which were all included in the kit were used. The serum samples were diluted 20 times with the dilution solution included in the kit and then dispensed in 50 μL per well into the antibody-immobilized plate, followed by reaction for one hour. Subsequently, the diluted samples were discarded, the plate was washed with the washing solution, and 50 μL of the biotinylated anti-pancreatic amylase antibody diluted with the dilution solution was dispensed into each well of the plate for another one hour of reaction. Furthermore, the biotinylated anti-pancreatic amylase antibody solution was discarded and the plate was washed with the washing solution. The POD-streptavidin conjugate diluted with the dilution solution was dispensed in 50 μL per well for 30 minutes of reaction. Subsequently, the POD-streptavidin conjugate solution was discarded and the plate was washed with the washing solution and, then, 50 μL of chromogen-substrate solution was added to each well. After 15 minutes of reaction, a stop solution was dispensed in 50 μL per well to stop the reaction and the absorbance at 450 nm was measured. A standard curve was generated based on the measured values of the pancreatic amylase standard for generating a standard curve, based on which the concentration of pancreatic amylase in serum was calculated for each sample from the obtained measured value.

The concentrations of the APOA2-ATQ protein, the APOA2-AT protein and pancreatic amylase in serum from each of the pancreatic ductal carcinoma patients represented by Samples A to F and the ranges of concentrations of those items in 10 samples from the healthy subjects are shown in Table 1. The concentrations of the APOA2-ATQ protein, the APOA2-AT protein and pancreatic amylase were measured in 10 samples from the healthy subjects and the means±1 SD of those measured values are presented as the ranges of concentrations in the healthy subjects.

The concentration of pancreatic amylase in the samples from the pancreatic exocrine dysfunction patients tends to deviate from the range of concentration derived from the healthy subjects. When the concentration of pancreatic amylase is below the range of concentration derived from the healthy subjects, the pancreatic exocrine dysfunction can be evaluated as insufficient production of pancreatic juice. When the concentration of pancreatic amylase is above the range of concentration, the pancreatic exocrine dysfunction can be evaluated as disturbance of pancreatic juice flow.

From the measurements on the healthy subjects, the concentration of pancreatic amylase in the healthy subjects was found to be in the range of 65.7 to 177.4 (U/L). On the other hand, it was found in the sample patients with pancreatic ductal carcinoma that a concentration below the range of concentration in the healthy subjects was observed in Samples A, B, and C while a concentration above the range of concentration was observed in Sample D. Consequently, it was found that the concentration of pancreatic amylase allowed the detection of reduced production of pancreatic juice in Samples A, B, and C and disturbance of pancreatic juice flow in Sample D. However, the measured values from Samples E and F stayed in the reference interval for the healthy subjects, suggesting that pancreatic exocrine dysfunction was not detectable based on the measured values of pancreatic amylase in those samples.

On the other hand, the concentrations of the APOA2-ATQ protein and the APOA2-AT protein in the healthy subjects were found to be in the range of 26.8 to 76.4 µg/mL and in the range of 22.7 to 158.3 µg/mL, respectively.

In the measurements using the samples from the pancreatic ductal carcinoma patients, the concentration of the APOA2-ATQ protein in Sample D from a pancreatic ductal carcinoma patient was below the range of concentration in the healthy subjects. Thus, we successfully determined that the subject represented by this sample had pancreatic exocrine dysfunction caused by disturbance of pancreatic juice flow. Furthermore, in Samples A to C, E and F from pancreatic ductal carcinoma patients, the concentration of the APOA2-ATQ protein was equal to or more than that in the healthy subjects while the concentration of the APOA2-AT protein was below the range of concentration in the healthy subjects. Thus, we successfully determined that the subjects represented by these samples had pancreatic exocrine dysfunction caused by insufficient production of pancreatic juice.

According to the above results, the use of the APOA2-AT protein and the APOA2-ATQ protein allowed the possibility of pancreatic exocrine dysfunction to be indicated even in the samples represented by Samples E and F, in which pancreatic exocrine dysfunction was not detectable by the method using pancreatic amylase. This indicates that test subjects who can be medically determined to have pancreatic exocrine dysfunction by a tube test may easily be selected by the detection method according to the present invention.

TABLE 1

| Samples | Concentration of APOA2-ATQ (µg/mL) | Concentration of APOA2-AT (µg/mL) | Concentration of amylase in blood (U/L) |
| --- | --- | --- | --- |
| Sample A | 114.5 | 4.3 | 33.3 |
| Sample B | 111.0 | 0.6 | 18.2 |
| Sample C | 122.4 | 0.3 | 8.0 |
| Sample D | 0.6 | 92.7 | 303.4 |
| Sample E | 91.6 | 8.7 | 97.4 |

TABLE 1-continued

| Samples | Concentration of APOA2-ATQ (µg/mL) | Concentration of APOA2-AT (µg/mL) | Concentration of amylase in blood (U/L) |
| --- | --- | --- | --- |
| Sample F | 101.3 | 6.3 | 70.1 |
| The average for 10 samples from healthy subjects | 51.6 | 90.5 | 121.55 |
| The range of concentration for 10 samples from healthy subjects | 26.8 to 76.4 | 22.7 to 158.3 | 65.7 to 177.4 |

Example 2: Detection of Pancreatic Exocrine Dysfunction by Using the APOA2-ATQ Protein or the APOA2-AT Protein in Blood as a Biomarker (2)

The relationship between the amounts of the indicated two APOA2 protein variants and the concentration of pancreatic amylase in plasma obtained from patients with chronic pancreatitis was examined.

Plasma samples collected with informed consent from 8 patients who had been diagnosed with chronic pancreatitis by an imaging examination (Samples G to N) and 60 healthy subjects were measured by ELISA for the concentrations of the APOA2-ATQ protein and the APOA2-AT protein to compare the result to the detection method for pancreatic exocrine function based on the concentration of pancreatic amylase. The measurement of the amount of each APOA2 protein or enzyme was performed according to a method similar to that in Example 1.

The concentrations of the APOA2-ATQ protein, the APOA2-AT protein and pancreatic amylase in plasma from each of the chronic pancreatitis patients represented by Samples G to N, are shown in Table 2. The concentrations of the APOA2-ATQ protein, the APOA2-AT protein and pancreatic amylase were measured in 60 samples from the healthy subjects and the means±1 SD of those measured values are presented as the ranges of concentrations in the healthy subjects.

The concentration of pancreatic amylase in the healthy subjects was found to be in the range of 38.7 to 85.9 (U/L). On the other hand, it was found in the sample patients with chronic pancreatitis that a concentration below the range of concentration in the healthy subjects was observed in Sample L and, moreover, a concentration above the range of concentration was observed in Samples H, J, and M. Consequently, it was found that the concentration of pancreatic amylase allowed the detection of reduced production of pancreatic juice in Sample L and disturbance of pancreatic juice flow in Samples H, J, and M. However, the measured values from Samples G, I, K, and N stayed in the reference interval for the healthy subjects, suggesting that pancreatic exocrine dysfunction was not detectable based on the measured values of pancreatic amylase in those samples.

On the other hand, the concentrations of the APOA2-ATQ protein and the APOA2-AT protein in the healthy subjects were found to be in the range of 32.9 to 85.8 µg/mL and in the range of 28.9 to 151.5 µg/mL, respectively.

In the measurements using the samples from the chronic pancreatitis patients, the concentration of the APOA2-ATQ protein in Samples H, J, and M from chronic pancreatitis patients was below the range of concentration in the healthy subjects. Thus, we successfully determined that the subjects represented by these samples had pancreatic exocrine dysfunction caused by disturbance of pancreatic juice flow. Furthermore, in Samples G, I, K, L, and N from chronic pancreatitis patients, the concentration of the APOA2-ATQ protein was equal to or more than that in the healthy subjects while the concentration of the APOA2-AT protein was below the range of concentration in the healthy subjects. Thus, we successfully determined that the subjects represented by these samples had pancreatic exocrine dysfunction caused by insufficient production of pancreatic juice.

According to the above results, the use of the APOA2-AT protein and the APOA2-ATQ protein allowed the possibility of pancreatic exocrine dysfunction to be indicated even in the samples represented by Samples G, I, K, and N, in which pancreatic exocrine dysfunction was not detectable by the method using pancreatic amylase. This indicates that test subjects who can be medically determined to have pancreatic exocrine dysfunction by a tube test may easily be selected by the detection method according to the present invention.

TABLE 2

| Samples | APOA2-ATQ (μg/mL) | APOA2-AT (μg/mL) | Concentration of amylase in blood (U/L) |
| --- | --- | --- | --- |
| Sample G | 151.2 | 2.2 | 41.1 |
| Sample H | 1.7 | 23.3 | 412.2 |
| Sample I | 112.9 | 1.2 | 46.1 |
| Sample J | 27.6 | 89.3 | 151.8 |
| Sample K | 193.1 | 0.8 | 39.7 |

TABLE 2-continued

| Samples | APOA2-ATQ (μg/mL) | APOA2-AT (μg/mL) | Concentration of amylase in blood (U/L) |
| --- | --- | --- | --- |
| Sample L | 121.7 | 4.4 | 27.8 |
| Sample M | 1.7 | 489.6 | 321.3 |
| Sample N | 67.3 | 12.2 | 51.3 |
| The average for 60 samples from healthy subjects | 59.4 | 90.2 | 62.3 |
| The range of concentration for 60 samples from healthy subjects | 32.9 to 85.8 | 28.9 to 151.5 | 38.7 to 85.9 |

INDUSTRIAL APPLICABILITY

According to the present invention, pancreatic exocrine dysfunction can effectively be detected by a simple test method imposing a lesser burden on a subject, which consequently allows weak abnormalities in pancreatic exocrine function to be detected, diagnosed and treated. Moreover, according to the method of the present invention, pancreatic exocrine dysfunction can be detected non-invasively by using blood, which consequently allows pancreatic exocrine dysfunction to be simply and quickly detected.

All publications, patents and patent applications cited in this specification shall be directly incorporated in this specification by reference.

The invention claimed is:

1. A method for detecting disturbance of pancreatic juice flow, the method comprising; determining an amount of APOA2-ATQ protein present in a test body fluid sample from a test subject and in a control body fluid sample from a normal subject by using an anti-APOA2-ATQ terminus antibody which specifically binds to the C-terminal region of the APOA2-ATQ protein consisting of the amino acid sequence represented by SEQ ID NO: 1, and an anti-APOA2 non-terminus antibody which binds to the amino acid sequence of the protein excluding the C-terminal region, wherein the determining process comprises the following steps (a) to (c);
 (a) contacting step of contacting the APOA2-ATQ protein present in the test body fluid sample and in the control body fluid sample with the anti-APOA2 non-terminus antibody, followed by contacting the APOA2-ATQ protein with the anti-APOA2-ATQ terminus antibody;
 (b) measuring step of measuring an amount of the APOA2-ATQ protein binding to both the anti-APOA2 non-terminus antibody and the anti-APOA2-ATQ terminus antibody in each of the test body fluid sample and the control body fluid sample; and
 (c) comparing step of comparing the amount of the APOA2-ATQ protein in the test body fluid sample with that in the control body fluid sample to determine whether or not the test subject has a pancreas affected by disturbance of pancreatic juice flow, wherein the anti-APOA2-ATQ terminus antibody comprises the CD:Rs shown in the following (i) or (ii);
 (i) in the heavy chain, CDR1, CDR2, and CDR3 having the amino acid sequence represented by SEQ ID NOs: 3, 4, and 5, respectively, and in the light chain, CDR1, CDR2, and CDR3 having the amino acid sequence represented by SEQ ID NOs: 6, 7, and 8, respectively, or
 (ii) in the heavy chain, CDR1, CDR2, and CDR3 having the amino acid sequence represented by SEQ ID NOs: 9, 10, and 11, respectively, and in the light Chain, CDR1, CDR2, and CDR3 having the amino acid sequence represented by SEQ ILS NOs: 12, 13, and 14, respectively, and wherein the anti-APOA2 non-terminus antibody comprises the CDRs shown in the following (iii) or (iv);
 (iii) in the heavy chain, CDR1, CDR2, and CDR3 having the amino acid sequence represented by SEQ ID NOs: 15, 16, and 17, respectively, and in the light chain, CDR1, CDR2, and CDR3 having the amino acid sequence represented by SEQ ID NOs: 18, 19, and 20, respectively, or
 (iv) in the heavy chain, CDR1, CDR2, and CDR3 having the amino acid sequence represented by SEQ ID NOs: 21, 22, and 23, respectively, and in the light chain, CDR1, CDR2, and CDR3 having the amino acid sequence represented by SEQ ILS NOs: 24, 25, and 26, respectively.

2. The method for detecting disturbance of pancreatic juice flow according to claim 1, wherein both the test body fluid sample and the control body fluid sample are blood.

3. The method for detecting disturbance of pancreatic juice flow according to claim 1, wherein, when the amount of the APOA2-ATQ protein of the test subject is smaller than that of the normal subject, the test subject is evaluated to have the pancreas affected by disturbance of pancreatic juice flow.

4. The method for detecting disturbance of pancreatic juice flow according to claim 2, wherein, when the amount of the APOA2-ATQ protein of the test subject is smaller than that of the normal subject, the test subject is evaluated to have the pancreas affected by disturbance of pancreatic juice flow.

5. The method for detecting disturbance of pancreatic juice flow according to claim 3, wherein the amount of the APOA2-ATQ protein of the test subject is no more than half of that of the normal subject.

6. The method for detecting disturbance of pancreatic juice flow according to claim 4, wherein the amount of the APOA2-ATQ protein of the test subject is no more than half of that of the normal subject.

* * * * *

UNITED STATES PATENT AND TRADEMARK OFFICE
CERTIFICATE OF CORRECTION

PATENT NO. : 11,162,956 B2
APPLICATION NO. : 15/555031
DATED : November 2, 2021
INVENTOR(S) : Michimoto Kobayashi et al.

It is certified that error appears in the above-identified patent and that said Letters Patent is hereby corrected as shown below:

In the Claims

In Claim 1, Column 45, Line 61, "CD:Rs" should read -- CDRs --
In Claim 1, Column 46, Line 35, "SEQ ILS NOs:" should read -- SEQ ID NOs: --
In Claim 1, Column 46, Line 50, "SEQ ILS NOs:" should read -- SEQ ID NOs: --

Signed and Sealed this
Eighteenth Day of October, 2022

Katherine Kelly Vidal
*Director of the United States Patent and Trademark Office*